(12) United States Patent
Ganem et al.

(10) Patent No.: US 8,360,057 B2
(45) Date of Patent: *Jan. 29, 2013

(54) MEDICATION INHALER FOR DISPENSING MULTIPLE CAPSULES

(75) Inventors: Charles F. Ganem, Cape Neddick, ME (US); Jake Ganem, Cape Neddick, ME (US); Scott Ganem, Cape Neddick, ME (US)

(73) Assignee: Dose One, LLC, Cape Neddick, ME (US)

( * ) Notice: Subject to any disclaimer, the term of this patent is extended or adjusted under 35 U.S.C. 154(b) by 133 days.

This patent is subject to a terminal disclaimer.

(21) Appl. No.: 13/051,522

(22) Filed: Mar. 18, 2011

(65) Prior Publication Data

US 2011/0220106 A1    Sep. 15, 2011

Related U.S. Application Data

(63) Continuation-in-part of application No. 12/530,365, filed as application No. PCT/US2007/019596 on Sep. 7, 2007, which is a continuation-in-part of application No. 11/716,204, filed on Mar. 9, 2007, now Pat. No. 7,832,399.

(60) Provisional application No. 60/781,265, filed on Mar. 10, 2006.

(51) Int. Cl.
   *A61M 15/00* (2006.01)
   *A61M 13/00* (2006.01)

(52) U.S. Cl. ......... 128/203.21; 128/203.12; 128/203.15; 128/203.23; 604/58

(58) Field of Classification Search ............. 128/200.21, 128/203.12, 203.15, 203.21, 203.23, 203.24; 222/80; 604/23, 24, 26, 57, 58, 183, 201–206, 604/272–274

See application file for complete search history.

(56) References Cited

U.S. PATENT DOCUMENTS

| | | | |
|---|---|---|---|
| 1,406,903 A | | 2/1922 | Rose |
| 2,037,986 A | | 1/1943 | Bolte et al. |
| 4,014,336 A | | 3/1977 | Mathes |
| 4,045,525 A | | 8/1977 | Huggins |
| 4,116,195 A | * | 9/1978 | James ........................... 604/244 |
| 4,338,931 A | * | 7/1982 | Cavazza ................... 128/203.15 |
| 4,423,724 A | | 1/1984 | Young |
| 5,048,514 A | * | 9/1991 | Ramella .................... 128/203.21 |
| 5,263,475 A | | 11/1993 | Altermatt et al. |
| 5,372,128 A | | 12/1994 | Haber et al. |
| 5,647,349 A | | 7/1997 | Ohki et al. |
| 5,673,686 A | * | 10/1997 | Villax et al. ............. 128/203.15 |
| 5,715,811 A | | 2/1998 | Ohki et al. |
| 5,848,994 A | | 12/1998 | Richmond |
| 5,868,721 A | | 2/1999 | Marinacci et al. |
| 5,881,721 A | * | 3/1999 | Bunce et al. ............. 128/203.21 |
| 6,186,141 B1 | | 2/2001 | Pike et al. |
| 6,280,424 B1 | | 8/2001 | Chang et al. |
| 6,488,027 B1 | | 12/2002 | Moulin |
| 6,613,026 B1 | | 9/2003 | Palasis et al. |
| 6,637,430 B1 | | 10/2003 | Voges et al. |
| 6,766,799 B2 | | 7/2004 | Edwards et al. |
| 6,892,727 B2 | | 5/2005 | Myrman |
| 6,923,175 B2 | | 8/2005 | Poole et al. |
| 6,941,947 B2 | | 9/2005 | Young et al. |
| 6,945,953 B2 | | 9/2005 | Wright |

(Continued)

*Primary Examiner* — Justine Yu
*Assistant Examiner* — LaToya M Louis
(74) *Attorney, Agent, or Firm* — Davis & Bujold, PLLC

(57) ABSTRACT

A medication inhaler for concurrently delivering multiple doses of medications including an inhaler body having a medication container chamber for receiving a plurality of medication containers and at least one air passage connecting the medication container chamber with external air, a mouthpiece axially engageable with the inhaler body and having a mouthpiece chamber for communication with a patient's respiratory system, and a hollow medication delivery needle communicating with the mouthpiece chamber. A medication delivery needle penetrates the medication containers when the inhaler is actuated and has at least one opening for passing exterior air and medication from interior spaces of the medication containers and through the needle to mouthpiece.

8 Claims, 24 Drawing Sheets

U.S. PATENT DOCUMENTS

| | | |
|---|---|---|
| 6,983,748 B2 | 1/2006 | Brown et al. |
| 7,220,266 B2 * | 5/2007 | Gambale ................. 606/144 |
| 7,645,268 B2 | 1/2010 | Mickley et al. |
| 7,666,172 B2 | 2/2010 | Atil |
| 2001/0020472 A1 * | 9/2001 | Horlin ................. 128/203.15 |
| 2002/0062829 A1 * | 5/2002 | Ohki et al. ............. 128/203.15 |
| 2003/0075172 A1 * | 4/2003 | Johnson et al. ......... 128/200.24 |
| 2003/0101995 A1 | 6/2003 | Yamashita et al. |
| 2003/0163099 A1 | 8/2003 | Wermeling et al. |
| 2003/0187404 A1 | 10/2003 | Waldenburg |
| 2005/0238708 A1 | 10/2005 | Jones et al. |
| 2006/0254583 A1 | 11/2006 | Deboeck et al. |
| 2006/0283448 A1 | 12/2006 | Edwards et al. |
| 2009/0090362 A1 | 4/2009 | Harmer et al. |
| 2009/0301471 A1 * | 12/2009 | Stirzel ................. 128/200.14 |

* cited by examiner

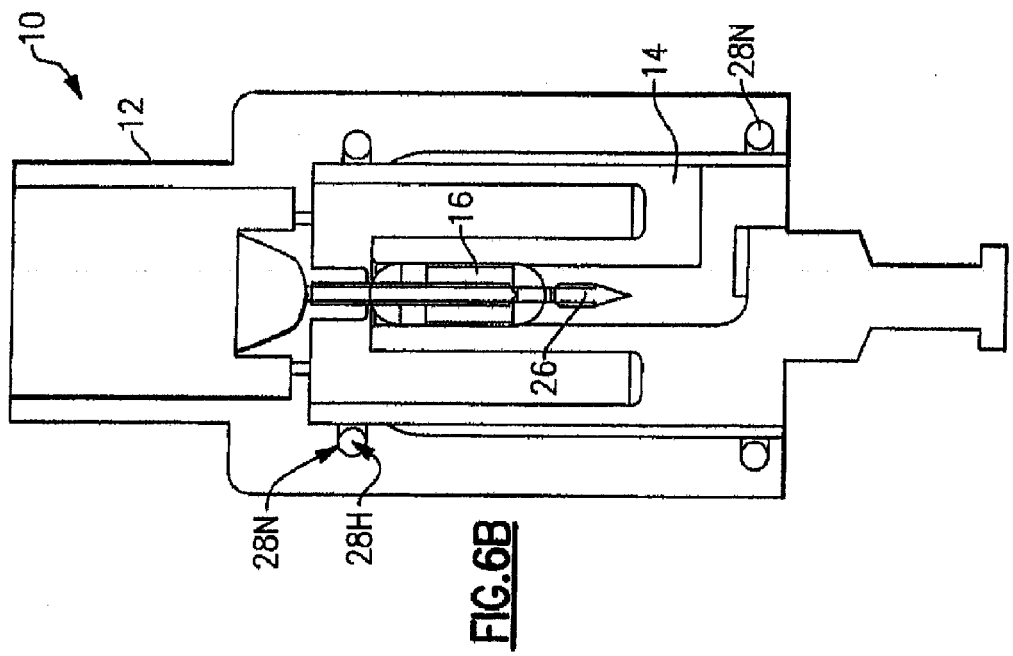
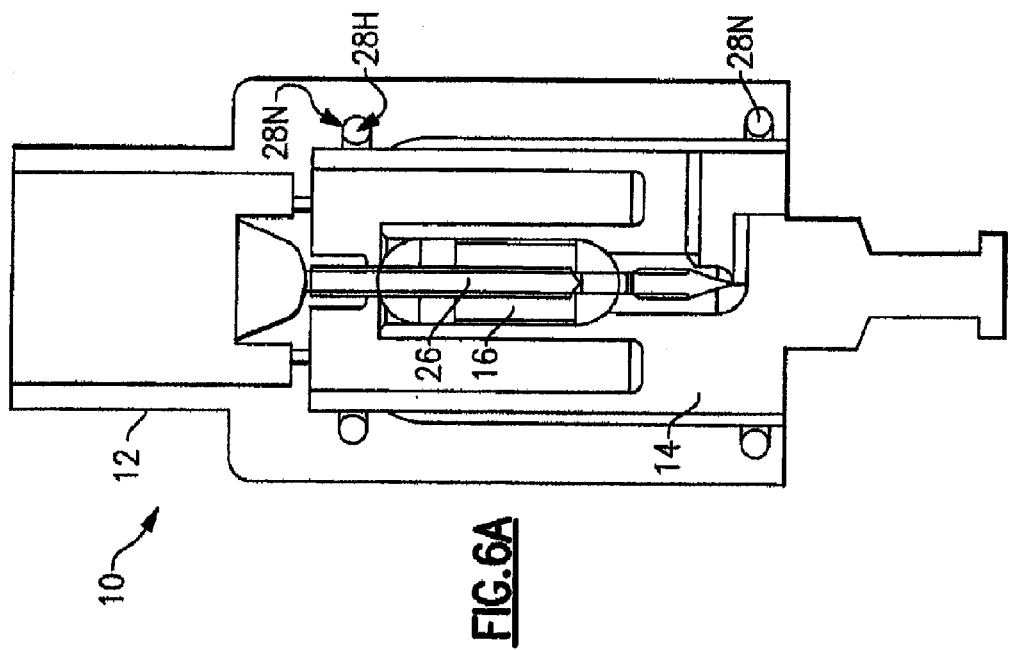

EMPTY HARD GELETIN CAPSULE PHYSICAL SPECIFICATIONS

| SIZE | OUTER DIAMETER (mm) | HEIGHT OR LOCKED LENGTH (mm) | ACTUAL VOLUME (mL) | TYPICAL FILL WEIGHTS (mg) 0.70 POWDER DENSITY |
|---|---|---|---|---|
| 000 | 9.91 | 26.14 | 1.37 | 960 |
| 00 | 8.53 | 23.30 | 0.95 | 665 |
| 0 | 7.65 | 21.70 | 0.68 | 475 |
| 1 | 6.91 | 19.40 | 0.50 | 350 |
| 2 | 6.35 | 18.00 | 0.37 | 260 |
| 3 | 5.82 | 15.90 | 0.30 | 210 |
| 4 | 5.31 | 14.30 | 0.21 | 145 |
| 5 | 4.91 | 11.10 | 0.13 | 90 |

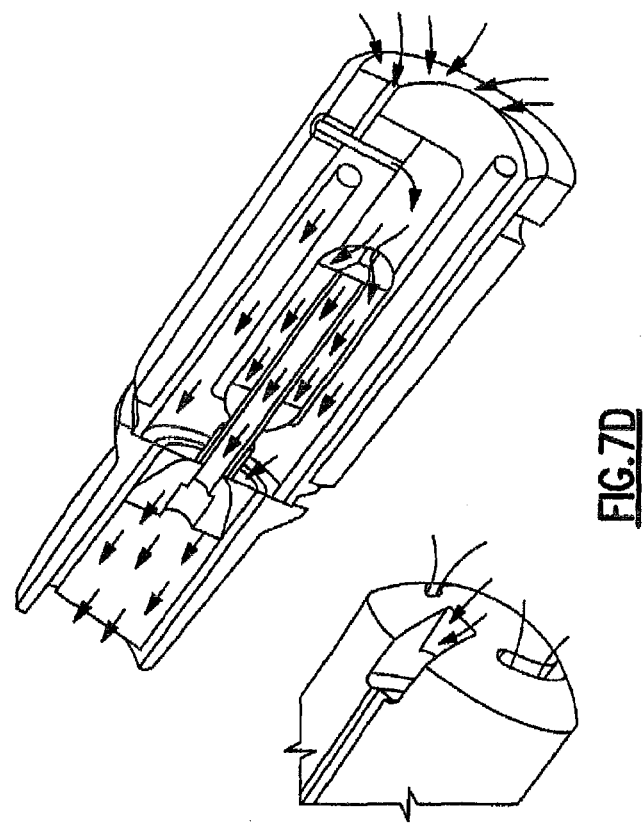
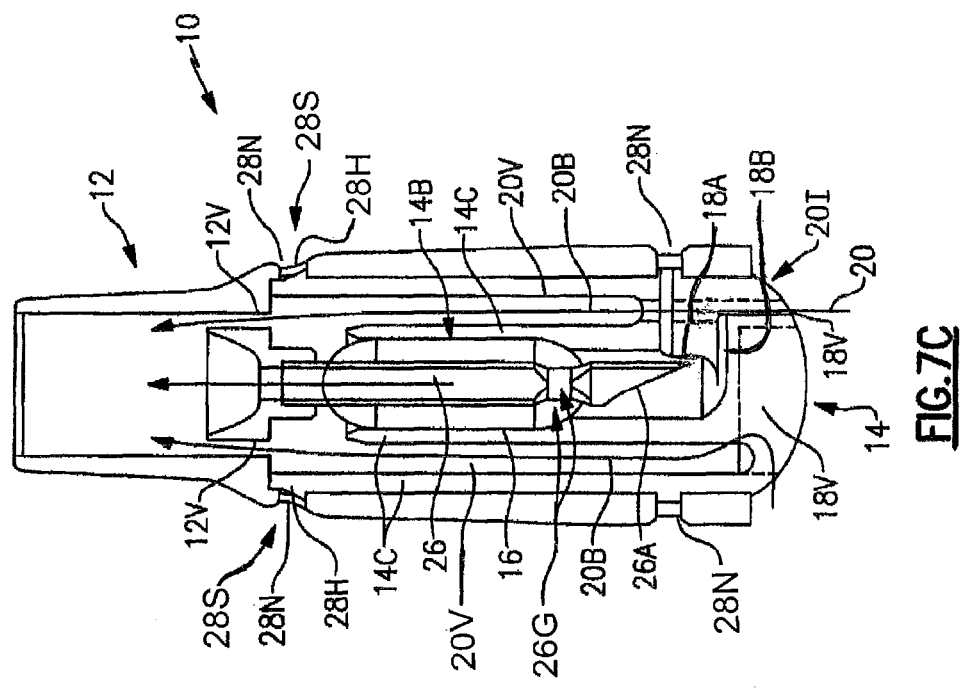
FIG. 7D
FIG. 7C

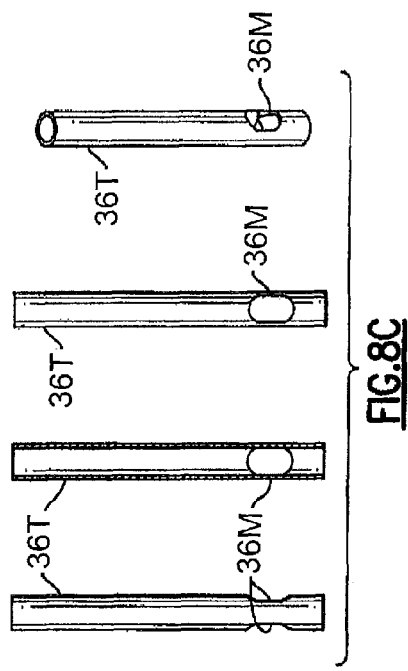
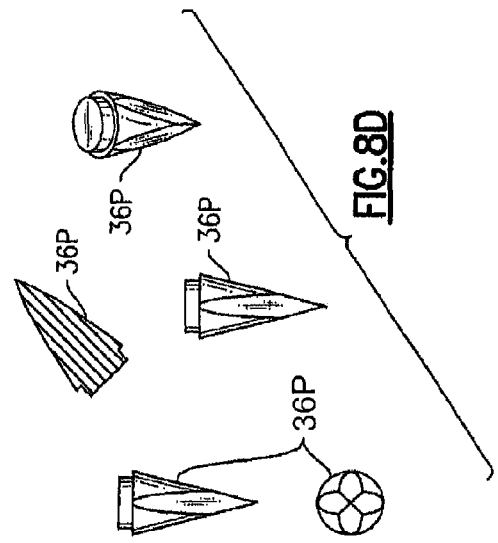
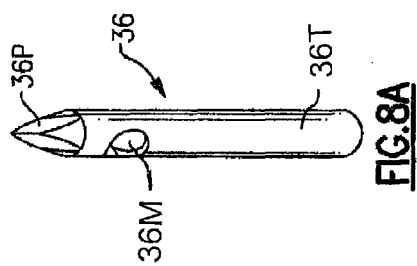
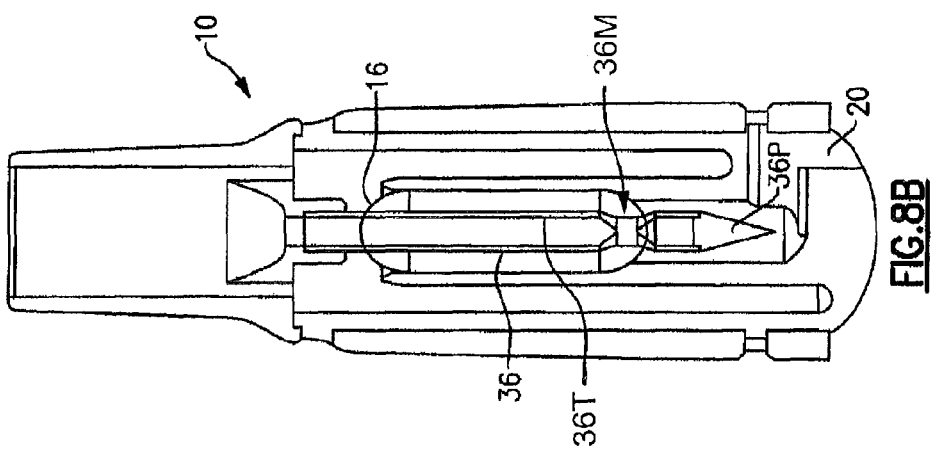

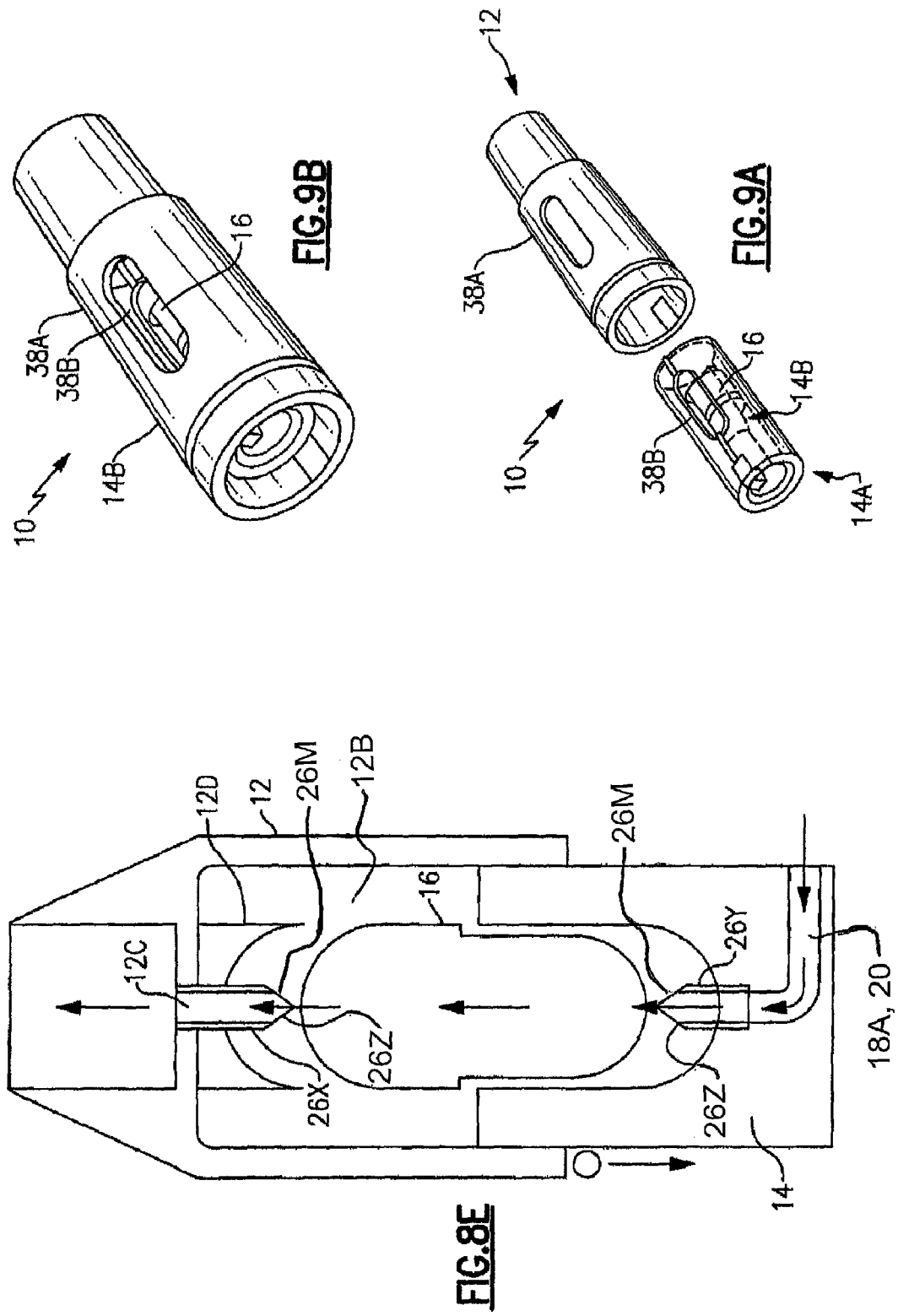

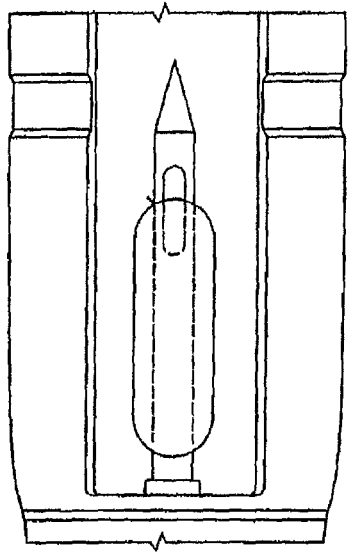
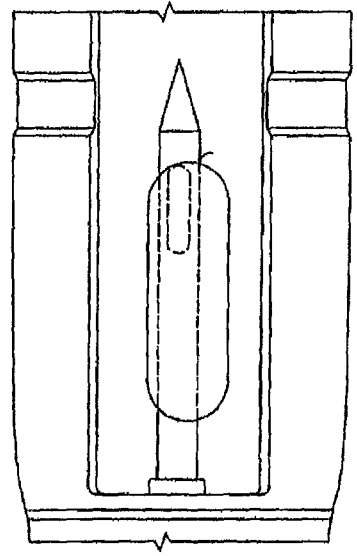
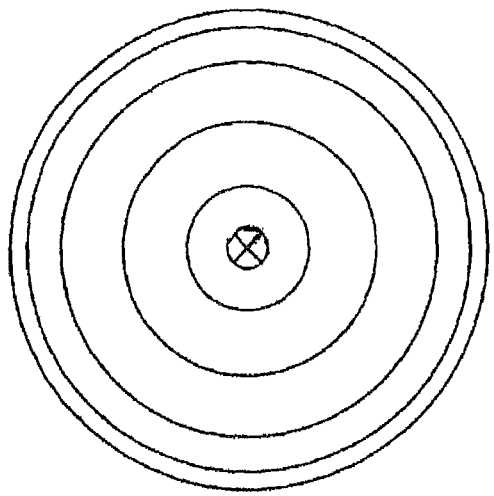
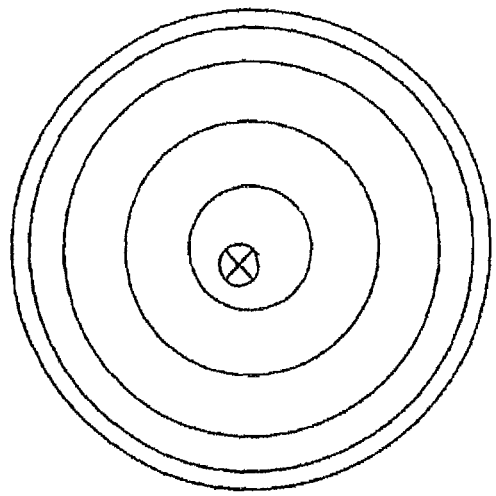
FIG.18B
FIG.18D
FIG.18A
FIG.18C

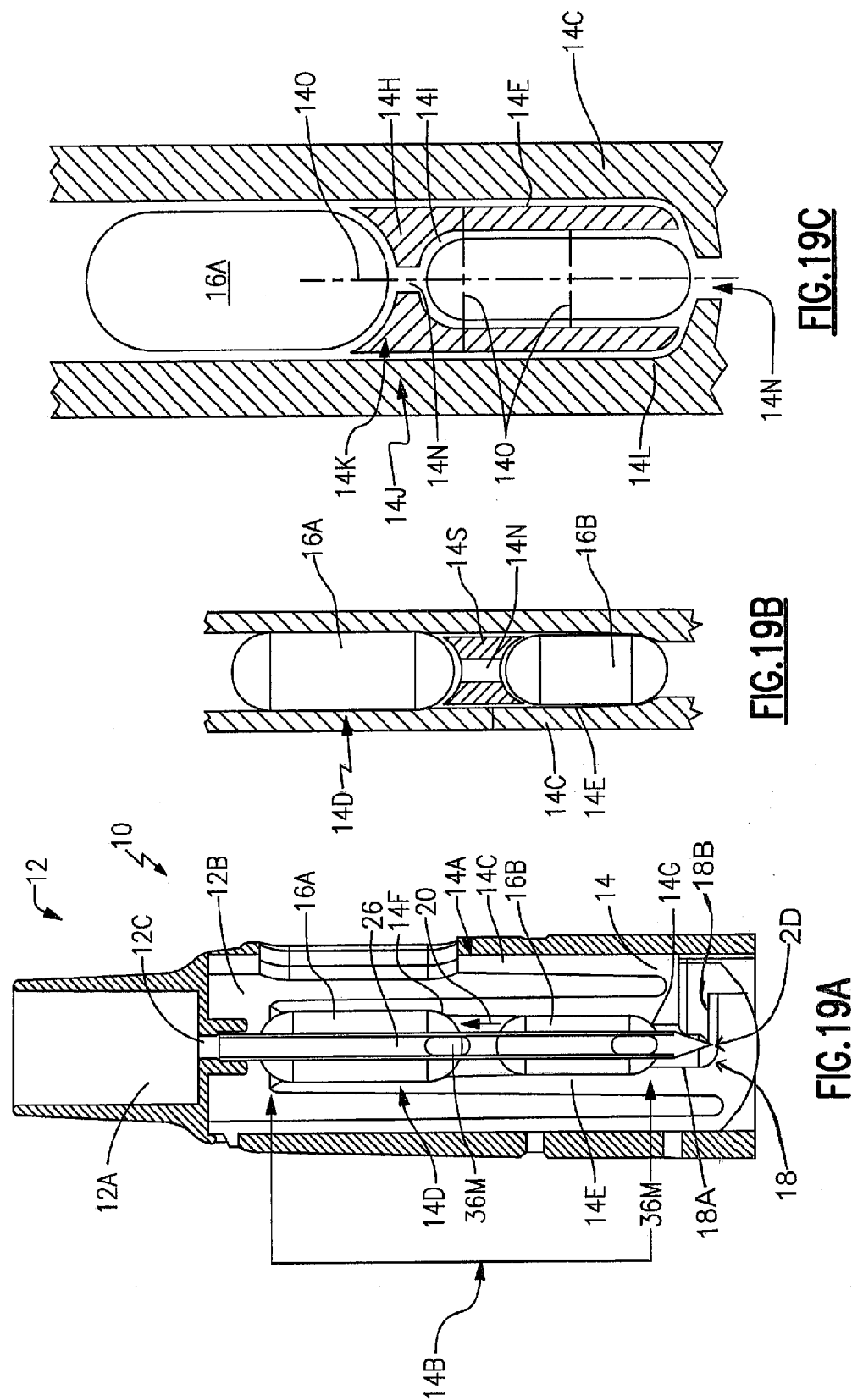

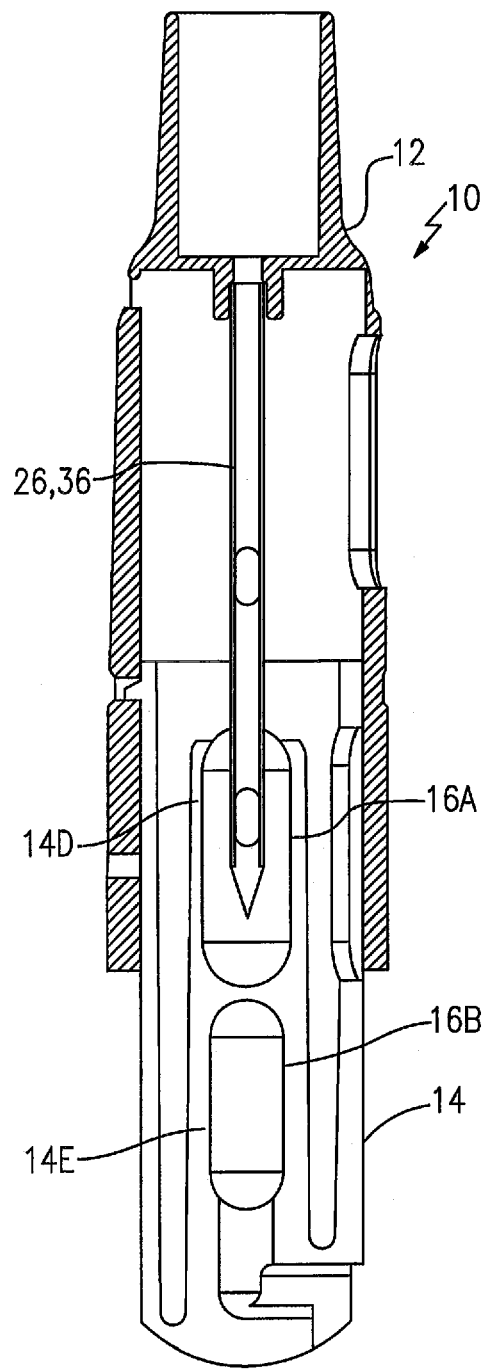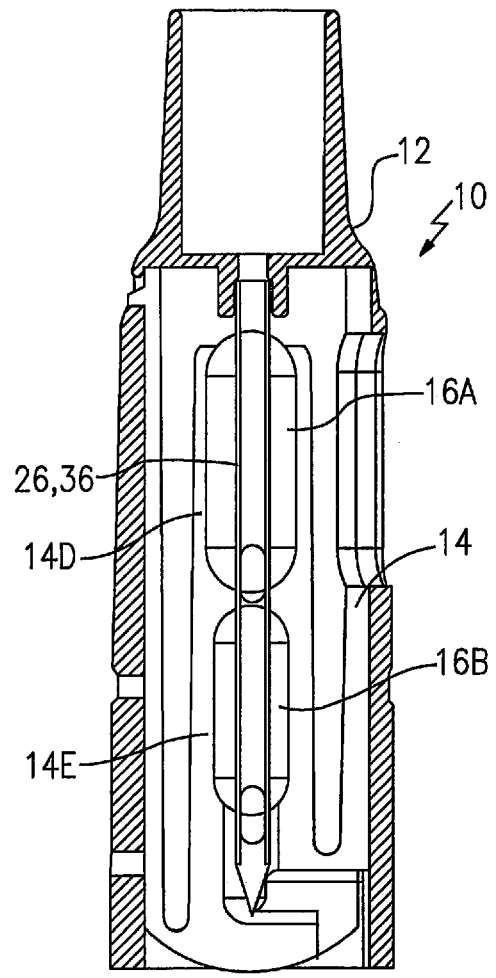
FIG.20C
FIG.20D

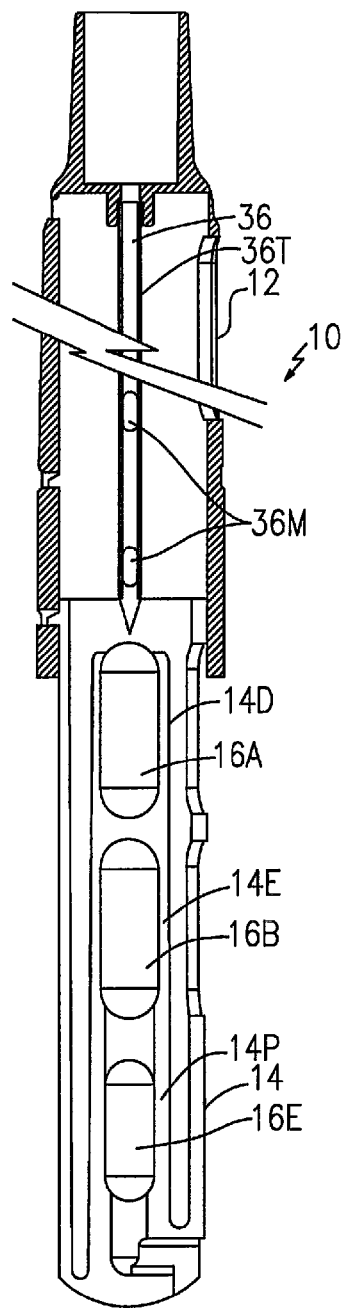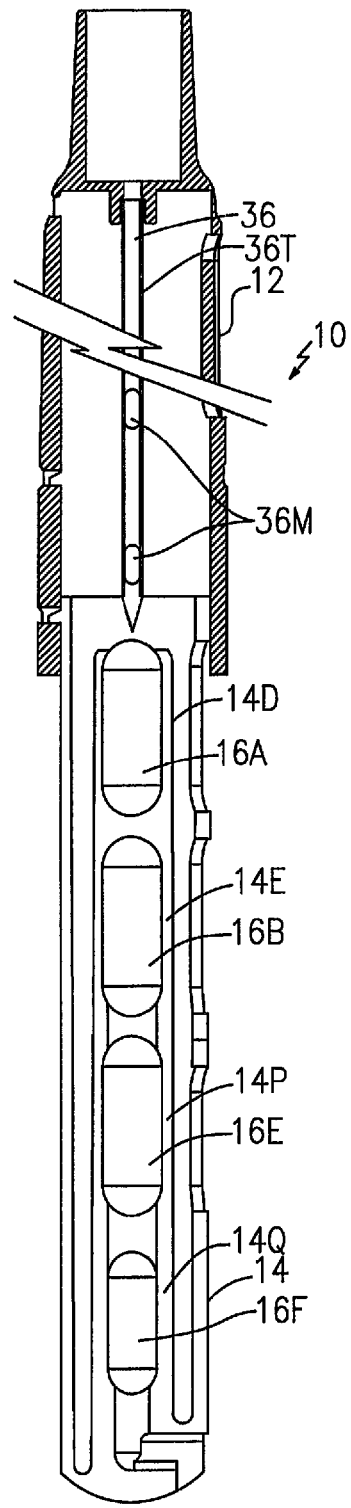
FIG.21A
FIG.21B

MEDICATION INHALER FOR DISPENSING MULTIPLE CAPSULES

This application is a continuation-in-part of and claims benefit of U.S. patent application Ser. No. 12/530,365 filed on Sep. 8, 2009 which is a national stage completion of PCT/US07/19596 file on Sep. 7, 2007 which is a continuation-in-part of and claims benefit of U.S. patent application Ser. No. 11/716,204 filed on Mar. 9, 2007 which is a continuation-in-part of and claims benefit of U.S. Provisional Application Ser. No. 60/781,265 filed on Mar. 10, 2006.

FIELD OF THE INVENTION

The present invention relates to an apparatus for administering medication in the form of a dry powder or a wet medication formulated to as a "dry" medication wherein the medication is formulated to be inhaled and, in particular, to an inhalation dispenser enclosing a sealed capsule of dry powdered or wet medication formulated as a "dry" medication with an air passage mechanism providing access to the capsule contents and an inhalation passage for inhalation of a mixture of air and the dry powder contents of the capsule.

BACKGROUND OF THE INVENTION

There are many medications that are formulated to be inhaled, including medications for respiratory diseases and problems and medications that are more easily and rapidly absorbed through the respiratory tissues. Such medications are often formulated as "mists", that is, aerosols of droplets suspended in air, but may also be in the form of fine, dry powders.

There are various forms of inhalers designed for the administration of such medications, but each offers a number of problems. For example, both wet and dry inhalers must incorporate features that provide safe, long term storage for the medications before they are used, typically by encapsulation of the medications in cartridges or capsules that are loaded into the devices when the medications are to be used. The encapsulated medications must then be "opened" safely and in a manner compatible with the dispensing of the medications, which requires that the medications continue to be retained within the capsule or container, but in such a way as to allow the medication to be dispensed to the patient.

The opening of a medication cartridge or capsule and the extraction of the medication may present particular problems, depending upon the type of medication and the type of cartridge or capsule. For example, cartridges or capsules containing wet medications commonly contain a pressurized propellant. The capsule seal must therefore safely and reliably retain the pressurized contents during storage, which in itself will typically make the seal more difficult to open, and further requires that the capsule seal and the opening mechanism be designed so as to retain the pressurized contents when the seal is breached during the opening process, which present additional difficulties.

Dry medications, however, present a different set of equally difficult requirements and dry powder inhalers of the prior art have employed a number of different types of medication containers, such as blister packs and reservoir storage mechanisms, all of which have been unsatisfactory in one aspect or another. More recent dry powder inhalers of the prior art have employed gelatin capsules, which share certain problems of the other prior art medication containers, such as a tendency for the medications to "clump" and thus be difficult to release from the container, and which present problems particular to gelatin capsules and similar medication containers. For example, one of the major problems of gelatin capsules has been the flaking or shearing of capsule particulate, that is, the production of particles or dust of the capsule material during puncture or destruction of the capsule to gain access to the medication therein. While the capsule material particulate is typically too large to be inhaled into the patient's lungs, the particulate often enters the patient's throat and causes at least some degree of discomfort. This problem is in some respects somewhat analogous to the problem of "coring" in hypodermic needles wherein a hypodermic needle may "core" out a cylinder or plug of tissue when inserted into the body of a patient, rather than opening a passage into the tissue, and wherein as a consequence the freed cored tissue may block the passage through the needle.

For these reasons, among others, inhalers tend to be relatively complex devices that are correspondingly often difficult to use and are generally relatively expensive to manufacture. These characteristics in turn largely limit the common use of medication inhalers to regions or countries of relatively high economic and educational levels where they will be administered and used by relatively highly qualified and trained medical personnel and by relatively highly educated patients able to afford and effectively use such devices. There is a significant need, however, for relatively inexpensive, easy to use medication inhalers in economically limited regions of the world and by people, including medical personnel, of relatively low educational levels, and preferably of a single use, throw away form having significantly reduced storage and use requirements.

The present invention addresses these and other problems of the prior art.

SUMMARY OF THE INVENTION

The present invention is directed to an apparatus for administering medication in the form of a dry powder or a wet medication formulated to as a "dry" medication wherein the medication is formulated to be inhaled and, in particular, to an inhalation dispenser enclosing a sealed medication container of dry powdered or wet medication formulated as a "dry" medication with an air passage mechanism providing access to the medication container contents and an inhalation passage for inhalation of a mixture of air and the dry powder contents of the medication container.

In particular, the present invention is directed to a dry medication inhaler that includes an inhaler body having a medication container chamber for receiving a medication container and at least one air passage connecting the medication container chamber with external air and a mouthpiece axially engageable with the inhaler body and having a mouthpiece chamber for communication with a patient's respiratory system and a hollow medication delivery needle communicating with the mouthpiece chamber. According to the present invention, the medication delivery needle extends toward the medication container chamber and has at least one opening for passing exterior air and medication from an interior space of a medication container in the medication container chamber through the needle and to mouthpiece chamber.

The mouthpiece engages with the inhaler body in a first position wherein the needle extends into the medication container chamber short of the medication container in the medication container chamber and in a second position wherein the needle axially traverses the medication container so that the at least one opening in the needle communicates with the at least one air passage and the interior space of the capsule in the medication container chamber.

The dry medication inhaler may also include a detent mechanism for retaining the mouthpiece and inhaler body in the first position for storing the inhaler with a medication container loaded into the medication container chamber and in the second position when the inhaler is actuated to delivery medication to the patient's respiratory system.

In one embodiment of the present invention, the medication delivery needle is a hollow cylindrical body terminating in a puncture point formed at an end of the needle toward the medication container chamber. A puncture plane extends obliquely across a diameter of the cylindrical body at an end of the needle toward the medication container to define the puncture point at the end of the needle and puncture edges extending along the plane of intersection between the puncture plane and the cylindrical body. The puncture edges form an oval opening into the interior of the needle and include cutting edges extending from the puncture point for a first part of the puncture edges and anti-coring edges for a second part of the puncture edges. When the mouthpiece and inhaler body are moved from the first position to the second position the puncture point establishes an initial opening through a wall of the medication container, the cutting edges penetrate the wall of the medication container and separate an attached flap of medication container material from the medication container wall, and the anti-coring edges contact the medication container wall and push the attached flap of medication container aside, thereby forming an opening through the medication container wall wherein the wall material of the opening remains as a flap attached to the medication container wall.

The medication delivery needle may also have at least one air/medication port located along the medication needle such that when the mouthpiece and inhaler body are in the second position the a first part of a length of the air/medication ports is located within the medication container and a second part of the length of the air/medication ports is located in connection with the air passage connecting the medication container chamber with the exterior air. In certain embodiments the medication needle may have one or more pairs of diametrically opposed air/medication ports.

In further aspects of the invention, the inhaler body may include at least one body vent passage located between the medication container chamber and an outer surface of the inhaler body and connected to the exterior air, and the mouthpiece may include at least one mouthpiece passage communicating between the at least one body vent passage and the mouthpiece chamber to provide a flow of exterior air into the mouthpiece chamber.

A presently preferred embodiment of the medication inhaler includes an inhaler body having a medication container chamber for receiving a medication container and at least one air passage connecting the medication container chamber with external air, a mouthpiece axially engageable with the inhaler body and having a mouthpiece chamber for communication with a patient's respiratory system, and a hollow medication delivery needle communicating with the mouthpiece chamber and extending toward the medication container chamber and having at least one opening for passing exterior air and medication from an interior space of a medication container in the medication container chamber through the needle and to mouthpiece chamber. Again, the mouthpiece engages with the inhaler body in a first position wherein the needle extends into the medication container chamber short of the medication container in the medication container chamber and in a second position wherein the needle axially traverses the medication container so that the at least one opening in the needle communicates with the at least one air passage and the interior space of the medication container in the medication container chamber.

In this presently preferred embodiment, the medication delivery needle includes a hollow, tubular body, a pyramidal puncturing point closing an end of the hollow, tubular body, and at least one pair of diametrically opposed air/medication ports located along the body so that when the mouthpiece and inhaler body are moved from the first position to the second position at least one air/medication port communicates with at least the at least one air passage and at least one air/medication port communicates with at least the interior space of the medication container. In addition, the inhaler body and the mouthpiece further include at least one body vent passage located between the medication container chamber and an outer surface of the inhaler body and connected to the exterior air and at least one mouthpiece passage communicating between the at least one body vent passage and the mouthpiece chamber to provide a flow of exterior air into the mouthpiece chamber.

In yet other embodiments of the inhaler of the present invention the pyramidal point of the needle may be oriented so that diametrically opposed vertices of faces of the pyramidal puncturing point are longitudinally aligned with the pair of air/medication ports, thereby reducing the possibility that the puncture flaps can interfere with the air/mediation ports. In other embodiments the air/medication ports are asymmetrically located along the needle body so that one is primary an inlet port and the other an outlet port.

In still other embodiments, the needle may additionally include a pair of rearward air/medication ports, spaced apart from the pair of air/medication ports in a direction away from the puncturing point of the needle to be positioned within the medication container when the mouthpiece engages with the inhaler body in the second position, and a baffle located within the hollow body of the needle between the pair of air/medication ports and the rearward pair of air medication ports.

In yet other embodiments the medication container may include at least one rear vent located at an end of the medication container opposite the puncturing point of the needle, or an exterior diameter of the needle located in a region extending inside and outside a rear wall of the medication container when the mouthpiece engages with the inhaler body may be reduced in diameter to form a rear vent between the exterior diameter of the needle and the wall of the medication container surrounding an opening by which the needle entered the medication container.

A further embodiment of the present invention is directed to a multiple concurrent dose medication inhaler having an inhaler body having at least first and second axially aligned medication chambers for each receiving first and second medication containers, at least one air passage connecting the first and the second medication container chambers with external air, and a mouthpiece axially engageable with the inhaler body and having a mouthpiece chamber for communication with a patient's respiratory system. A hollow medication delivery needle communicates with the mouthpiece chamber and extends toward the medication container chamber and has at least respective first and second openings spaced along the medication delivery needle for passing exterior air and medication from interior spaces of the first and second medication containers in the first and second medication container chambers through the needle and to mouthpiece chamber.

According to the present invention, the mouthpiece engages with the inhaler body and, in a first position, the needle extends toward but terminates short of both the first and the second medication containers located within the first and the second medication container chambers and, in a second position, the needle axially traverses both the first and the second medication containers so that the at least first and second openings in the needle respectively communicate with the at least one air passage and interior spaces of the first and the second medication containers in the first and second medication container chambers to convey the container contents to the mouthpiece.

In a presently preferred embodiment of a multiple concurrent dose medication inhaler, the medication delivery needle includes a hollow, tubular body and a pyramidal puncturing point closing an end of the hollow, tubular body and the body includes at least first and second air/medication ports located along the body so that when the mouthpiece and the inhaler body are moved from the first position to the second position, each of the at least first and second air/medication openings in the body communicates with both the at least one air passage and the interior space of a corresponding one of the at least first and second medication containers.

In further embodiments of the multiple concurrent dose medication inhaler the first medication container and the first container chamber may be of greater diameter than the second medication container and the second container chamber, or the first medication container and the first container chamber may be of generally equal or smaller diameter than the second medication container and the second container chamber. That is, the overall sizes and/or dimensions of both the first and the second container chambers can vary but are designed to receive a desire combination of containers to be dispensed.

For an embodiment of a multiple dose medication inhaler in which the first and the second container chambers are of generally equal diameter may further include a container spacer located between the first and the second medication containers where the container spacer is generally of a cylindrical shape with a diameter to be closely received in one of the first and the second container chambers and with opposed concave axial faces which are generally shaped to conform with ends of the first and the second medication containers, to be respectively accommodated within the first and the second container chambers, and have an axial needle passage which facilitates passage of the medication delivery needle through the container spacer.

In further embodiments of the multiple dose medication inhaler, the first and second medication containers and the first and second container chambers are generally of equal diameter or size, the medication inhaler may further include a container adapter located in one of the first and the second container chambers where the exterior surface of the container adapter is generally of a cylindrical shape with a diameter to be closely received in and axially supported within one of the first and the second container chambers and will also include a generally cylindrical internal container chamber having an internal diameter for closely receiving a desired medication container having a small diameter or size than the first or the second medication container so as to thereby facilitate supporting a medication container, having a smaller diameter or size, within one of the first and the second container chambers in axial alignment with the other of the first and second medication containers so as to be penetrated by the needle when the inhaler body is moved to its second position.

Regardless of the amount of medication container chambers which are contained, end-to-end in axial alignment with one another, within the multiple dose medication inhaler, it is important that each accommodated medication container be located within the respective medication container chamber so as to minimized any radial movement of the medication container, with respect to the respective medication container chamber, and thereby assist the needle with the penetrating each accommodated medication container, when the inhaler body is moved to its second position, for simultaneously dispensing of the entire contents of each accommodated medication container.

BRIEF DESCRIPTION OF THE DRAWINGS

The above discussed aspects of the prior art and the following discussed aspects of the present invention are illustrated in the figures, wherein:

FIGS. 6A and 6B illustrate adaptations of the inhaler for various sizes of medication containers;

FIGS. 7A-7D are diagrammatic illustrations of one presently preferred embodiment of the present invention with a first embodiment of a medication delivery needle;

FIGS. 8A-8E illustrate further embodiments of a medication delivery needle and inhaler;

FIGS. 9A and 9B illustrate an inhaler having container windows;

FIGS. 18A-18D are diagrammatic illustrations of centered and eccentric penetrations of a medication by a needle;

FIG. 19A is a diagrammatic sectional view of a multiple concurrent dose medication inhaler;

FIGS. 19B and 19C are diagrammatic partial sectional views of the medication container chambers and adapters of the multiple concurrent dose medication inhaler;

FIGS. 20A, 20B, 20C and 20D illustrated successive stages in the operation of a multiple concurrent dose medication inhaler;

FIG. 21A is a diagrammatic sectional view of the multiple concurrent dose medication inhaler having three medication chambers arranged end-to-end sequentially one after the other;

FIG. 21B is a diagrammatic sectional view of the multiple concurrent dose medication inhaler having four medication chambers arranged end-to-end sequentially one after the other.

DETAILED DESCRIPTION OF THE INVENTION

A. General Description of a Dry Medication Inhaler

Figure 1A:
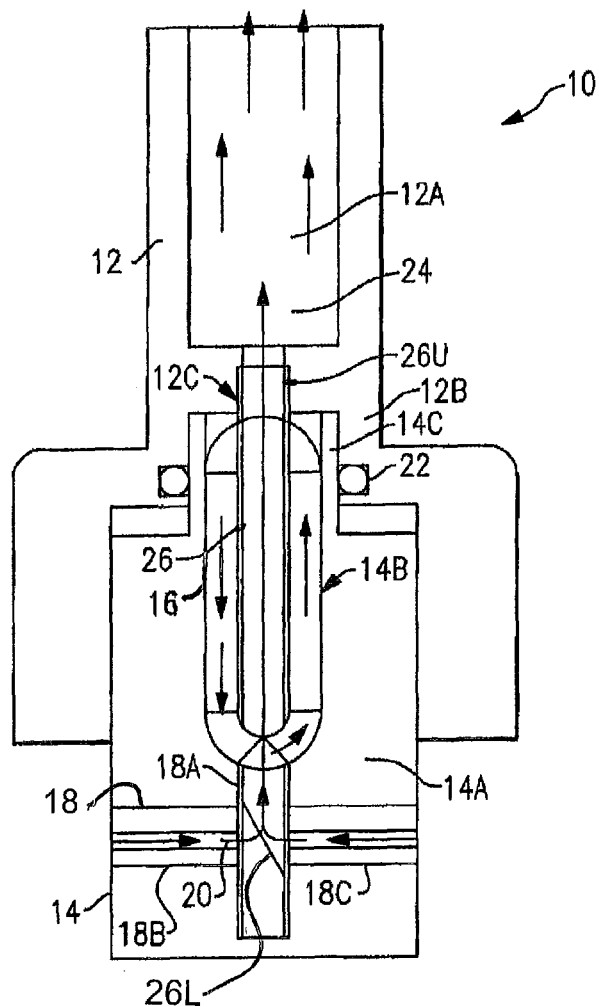
FIG. 1A is a diagrammatic representation of a dry medication inhaler according to one embodiment of the present invention.

Referring to FIG. 1A, therein is shown a diagrammatic representation of a dry medication inhaler 10 of the present invention wherein, as in all of the following figures unless stated otherwise, references to, for example, the "upper" or "lower" portions of an element will refer to the relative location and orientation of the elements in the Figures.

As represented FIG. 1A, a dry medication inhaler 10 includes a mouthpiece 12 and a body 14 enclosing a medication container 16. In a typical embodiment, mouthpiece 12 and body 14 may have, for example, generally cylindrical or oval external cross sections and the exterior cross section of the upper portion of mouthpiece 12 may be further shaped into, for example, a cross section that can be comfortably received into a patient's mouth.

Referring first to body 14, body 14 generally forms a structure for enclosing a medication container 16 and, as shown in FIG. 1A, typically has a cylindrical main body 14A that includes an axially extending container chamber 14B having a length and diameter sized and shaped to receive and enclose a medication container 16. The body 14 includes one or more air passages 18 for drawing air into and through the medication container 16, which are represented in the figure as including a lower vertical air passage 18A extending downwards from the bottom end of container chamber 14B and intersecting horizontally extending air passages 18B and 18C that connect with the air exterior to body 14 to provide a lower air passage 20 extending between the exterior air and into the bottom end of container chamber 14B. It should be noted, however, that the alternate configurations of lower air passages 18A, 18B, 18C and/or 20 may be used. For example, there may be only one air passage 18B or 18C intersecting lower vertical air passage 18A, there may be several air passages connecting between the outside air and lower vertical air passage 18A, rather than just one or two lower air passages 18B/18C. In yet other embodiments, one of more air passages 18B/18C may intersect lower vertical air passage 18A at a slant or slants, rather than at right angles, or lower vertical air passage 18A may extend in a straight path to connect with the outside air, or lower vertical air passage 18A or one or more air passages 18B/18C may connect with the outside air through a "torturous", curves or zig-zagged path or paths, rather than a straight path or paths. In yet other embodiments the air passage connection between lower vertical air passage 18A and the outside air may take the form of a slot or slots aligned parallel to, perpendicular to or at an angle or angles with lower vertical air passage 18A, and so on.

In the illustrated embodiment, body 14 includes a cylindrical wall 14C that surrounds container chamber 14B and that extends upwards above the upper end of container chamber 14B wherein, in the illustrated embodiment, the upward extension has an exterior diameter that is less than the exterior diameter of the main part of body 14A. As shown, the interior of cylindrical wall 14C forms an upward end of container chamber 14B, and, as discussed below, cylindrical wall 14C sealingly mates with a corresponding portion of mouthpiece 12. It should be recognized, however, as will be apparent from FIG. 1A and the following descriptions, that the exterior diameter of cylindrical wall 14C may, for example, be equal to that of main body 14A, with corresponding adaptations to the mating contours of mouthpiece 12.

Referring now to mouthpiece 12, mouthpiece 12 generally provides a mechanism for opening a medication container 16 residing in body 14 and for delivering the medication therein to a user. As illustrated in FIG. 1A, mouthpiece 12 includes two axially connected interior spaces, including a mouthpiece chamber 12A in the upper portion of mouthpiece 12 and a body chamber 12B in the lower portion of mouthpiece 12, with the two chambers being axially connected through a needle passage 12C. As shown, the interior of body chamber 12B and the lower part of needle passage 12C are shaped and sized to receive the upper portion of main body 14A and cylindrical wall 14C, thereby forming an enclosed protective container chamber 14B in which a medication container 16 can reside. The illustrated embodiment of the inhaler 10 may further include a ring seal 22, located in body chamber 12B, that seals against the outer diameter of cylindrical wall 14C to form a single medication passage 24 that extends from lower air passage 20, and through container chamber 14B and any container 16 residing therein, and through needle passage 12C to mouthpiece chamber 12A. In other embodiments, however, the seal may take the form of a surface to surface contact seal between the corresponding surfaces of main body 14A and mouthpiece 12, or a sealing function may not be required.

As also illustrated in FIG. 1A, mouthpiece 12 includes a hollow medication delivery needle 26 that functions to open the medication container 16, thereby making the medication accessible to the patient or user, and as a delivery mechanism for extracting the medication from the medication container 16 and delivering the medication to the user or patient. As shown, an upper section of medication delivery needle 26 resides in needle passage 12C, with the upper end 26U of medication delivery needle being located in the region of the intersection of needle passage 12C and mouthpiece chamber 12A. As will be shown in following discussions of alternate implementations, the upper end 26U of delivery needle 26 may be located over an axial range extending from within needle passage 12C to within mouthpiece chamber. As shown, and as discussed below, the lower end 26L of medication delivery needle 26 extends downwards to pierce medication container 16 and to form a passage for the delivery of the medication when mouthpiece 12 and main body 14 are axially telescoped into the activated position.

Figure 1B:
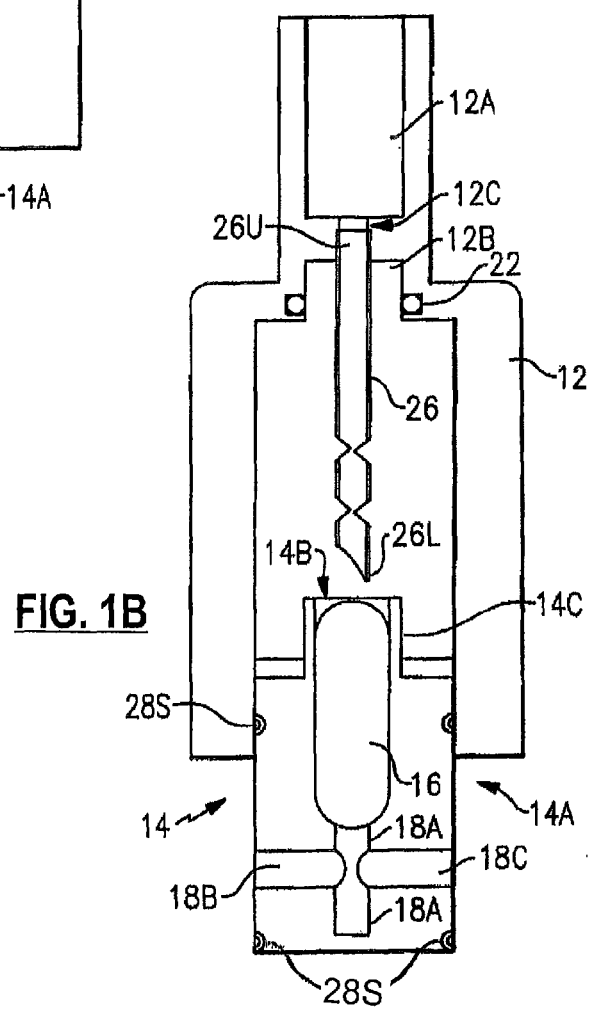
FIGS. 1B and 1C are diagrammatic illustrations of the stored and activated positions of an inhaler.
Figure 1C:
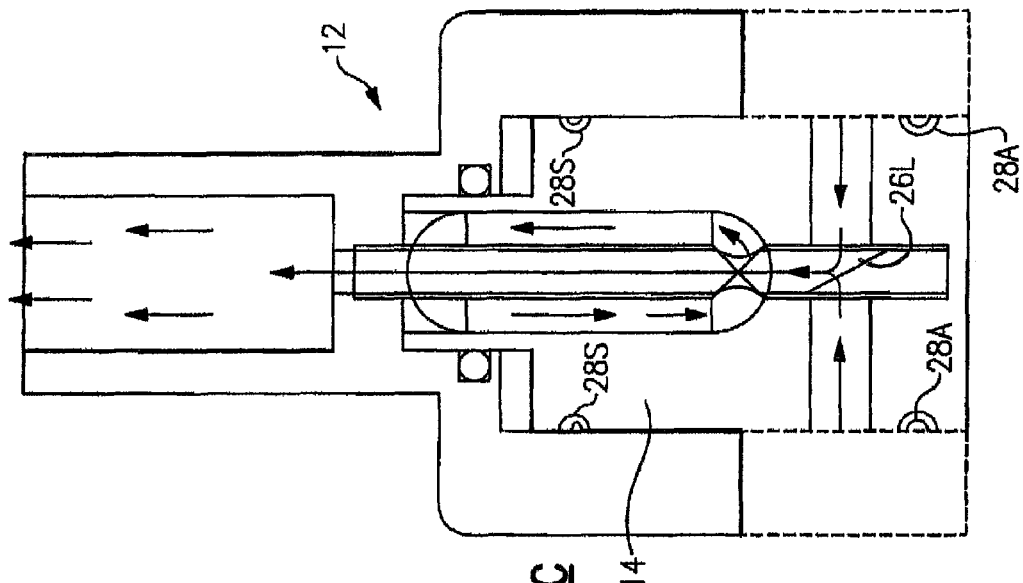

Therefore considering the use and operation of an inhaler 10, and as illustrated in FIGS. 1B and 1C for an embodiment of an inhaler 10, in an initial step a medication container 16 is inserted into container chamber 14B and mouthpiece 12 and main body 14 are fitted together to enclose the medication container 16, whereupon the inhaler 10 may be said to be in the "storage" state, that is, assembled with a medication container 16 but not yet activated to release the medication from the medication container 16.

When mouthpiece 12 is in the "storage" position with respect to main body 14, that is, when mouthpiece 12 is partially but not fully engaged with main body 14, as illustrated in FIG. 1B, the lower end 26L of delivery needle 26 will extend downwards from mouthpiece 12 and along the common axis of mouthpiece 12 and main body 14, to a point short of container chamber 14B and a medication container 16 residing in container chamber 14B.

At this point, the medical personnel administering the medication to a patient or the patient themselves, may activate the inhaler 10 to release and deliver the medication by pushing mouthpiece 12 and main body 14 together to the fully activated position. Once the medication has been administered to the patient, as discussed further below, the inhaler may be opened to remove and discard the expended container, and the inhaler subsequently prepared for another use by inserting a new container when needed. The inhaler 10 may thereby be employed as a multi-use device or, if discarded with the expended container after use, as a single use device, depending upon the particular requirements under which the inhaler 10 is employed.

In the alternative, however, the inhaler 10 can remain in the "storage" state for an extended period determined by the packing of the inhaler 10 or the medication container or containers therein, thereby allowing inhalers 10 to be prepared, stored and delivered as pre-loaded ready-to-use devices for the delivery of a particular medication. In this regard, it must be noted that medications are typically enclosed in an "overpack", that is, an additional air-tight packaging, to extend the storage life of the medications, and that the use life of medications once removed from the overpack is often limited to, for example, 30 days. These methods may be applied to pre-loaded inhalers 10 by, for example, enclosing the pre-loaded inhaler 10 in an overpack or by enclosing the medication containers themselves in individual overpacks within the inhaler 10 whereupon, for example, activation of the inhaler 10 mechanism would open the overpack as well as the container.

It should also be noted in this regard that, as will be described further in a following discussion, mouthpiece 12 may be engaged with main body 14 and retained in the storage position by, for example, corresponding circumferential detent rings and grooves on the matching corresponding interior/exterior surfaces of mouthpiece 12 and main body 14, or by any other equivalent detent mechanism 28S. In these implementations, therefore, a positive application of force along the common axis of mouthpiece 12 and main body 14 would be required to overcome the detent so that mouthpiece 12 could move to become fully engaged with main body 14, and a medication container 16 residing in container chamber 14B would remain sealed until such a force was applied.

In this regard, it must be noted that a number of alternative implementations may be employed to allow the storage detect function when the inhaler 10 is to be employed as a pre-loaded ready-to-use devices. For example, FIG. 1B illustrates an embodiment wherein the portion of mouthpiece 12 that encloses main body 14A when the inhaler 10 is in the "storage" configuration is extended so that the detent mechanism 28S located at the lower part of mouthpiece 12 engages an upper portion of main body 14 in such a manner that medication delivery needle 26 is held in a "storage" position short of contacting the container 16. In other embodiments, however, the necessary clearance between the medication delivery needle 26 and the container 16 may be achieved, for example, by a cylindrical body enclosing either or both of mouthpiece 12 and main body 14A and having a detent mechanism or mechanisms interacting with mouthpiece 12 and main body 14A.

Therefore, next considering the activation and activated state of an inhaler 10, as illustrated in FIG. 1C, the application of a sufficient axial force to mouthpiece 12 and main body 14 will cause mouthpiece 12 and main body 14 to move towards one another and into the fully activated position. This motion will result in delivery needle 26 being forced downwards through container chamber 14B and a medication container 16 residing therein, until delivery needle 26 extends through container chamber 14B and the medication container 16 and into lower vertical air passage 18A, until lower end 26L of delivery needle 26 is located in lower vertical air passage 18A at a point lower than horizontally extending air passages 18B and 18C.

The inhaler 10 is then In the fully activated, or engaged, position of the inhaler 10, wherein medication container 16 has been opened, or unsealed, to provide access to the medication therein, and an air passage has been formed that extends from air passage 20 and through the medication container 16, container chamber 14B, and needle passage 12C, and into mouthpiece chamber 12A.

At this point, it should be noted that mouthpiece 12 and main body 14 may include additional corresponding circumferential detent rings and grooves on their matching corresponding interior/exterior surfaces, or equivalent latching detent mechanisms 28S, to prevent the separation of mouthpiece 12 and main body 14 after the inhaler 10 has been activated. This feature would prevent the refilling and re-use of the inhaler, so that the inhaler 10 would be a single use, throw-away device, which would be particularly useful with relatively untrained or uneducated medical personnel or patients.

Figure 2A:
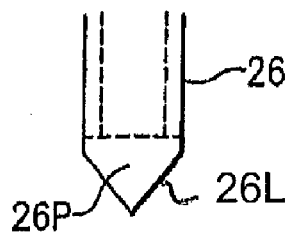
FIGS. 2A-2F are diagrammatic illustrations of possible implementations of a medication delivery needle.
Figure 2B:
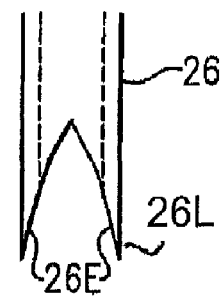
Figure 2C:
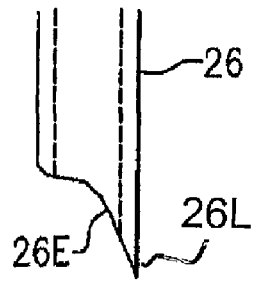
Figure 4:
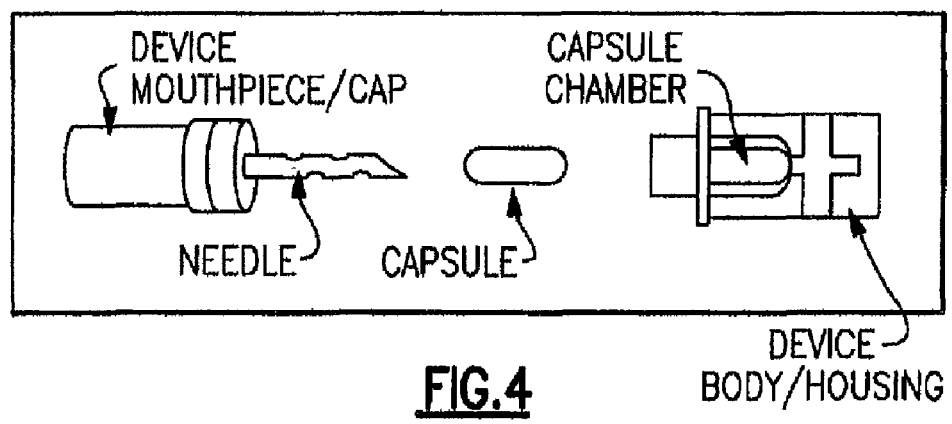
FIG. 4 is a disassembled view of an inhaler.

The operation of an inhaler 10 and the delivery needle 26 in delivering medication to the patient is illustrated in FIGS. 2A-2D, illustrate alternate embodiments of a delivery needle 26 and, in conjunction with FIGS. 1A-1C, the delivery of medication from a medication container 16 to a user. As shown in FIGS. 2A-2C, lower end 26L of a delivery needle 26 is shaped to facilitate the penetration of the delivery needle 26 into and through a medication container 16 residing in the container space 14B. For example, lower end 26L may be closed with a sharp, penetrating point 26P or may be shaped into single or double slanting edge 26E terminating in sharp points.

Figure 2F:
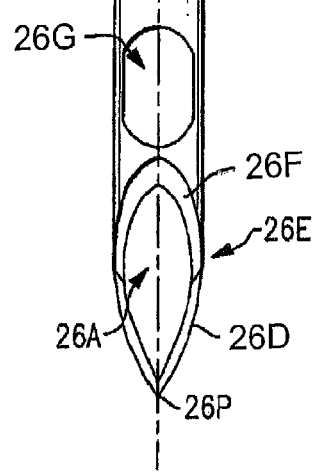
Figure 2D:
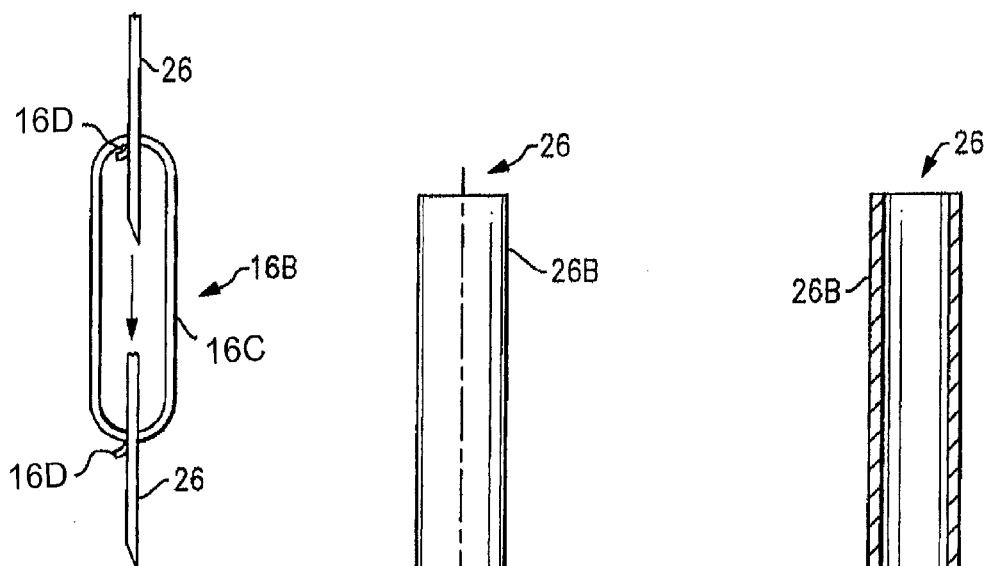
Figure 2E:
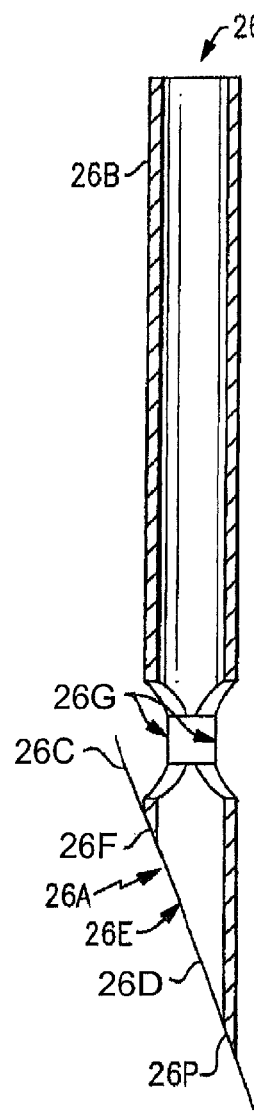

FIGS. 2D and 2E, in turn, illustrates a design of a delivery needle 26 that is particularly adapted to avoid the production of particles or dust of the container material during puncture or destruction of the container to gain access to the medication therein. FIG. 2F illustrates the operation of the delivery needle 26 on a medication container 16. As illustrated in FIG. 2D, the delivery needle 26 is comprised of a hollow generally cylindrical body 26B terminating in a puncture point 26P formed at the extreme end of body 26B by a puncture plane 26C that extends obliquely, that is, at a slant, across the diameter of body 26B at an angle of, for example, approximately 30° to the axis of body 26B. As shown, puncture plane 26C forms a generally oval or elliptically shaped opening into the interior of the needle wherein the edge or rim of the opening is defined by puncture edges 26E that extend along the intersections between body 26B and puncture plane 26C from puncture point 26P to a generally diametrically opposite point on body 26B that is located along body 26B at a distance away from puncture point 26P that is compatible with the angle of puncture plane 26C and the diameter of body 26B.

As indicated in FIGS. 2D and 2E, puncture edges 26E are formed of cutting edges 26D that extend from puncture point 26P and back along both sides of puncture edges 26E for a selected distance, such as approximately one half the length of puncture edges 26E. Puncture edges 26E are then continued by anti-coring edges 26F that extend along puncture edges 26E from the back end of cutting edges 26D to the rearmost point of puncture edge 26E, where puncture edges 26E rejoin at the outer surface of body 26B.

In use, and referring to FIGS. 2D, 2E and 2F, puncture point 26P establishes an initial opening or puncture into the material 16C of the medication container 16 and cutting edges 26D follow puncture point 26P into material 16C with a cutting action to begin separation of a flap 16D from the material 16C. The separation of flap 16D from material 16C will continue as delivery needle 26 continues to penetrate the material 16C of the medication container 16, and will continue until anti-coring edges 26F come into contact with the material 16C. At this point, delivery needle 26 will have cut out a flap 16D that will form an opening or hole through the material 16C of the container 16 wall, wherein the opening or hole may be of approximately the diameter of body 16B and may occupy approximately one half to two thirds of the circumference of body 16B, and wherein the flap 16D is attached to the material 16C of the wall of the container 16.

According to the present invention, anti-coring edges 26F are formed to have a non-cutting shape, such as a radius rather than a cutting edge, by, for example, grit blasting or polishing or swaging of the anti-coring edges 26F. As such, the cutting of flap 16D from the material 16C of the wall of the container 16 will cease when anti-coring edges 26F enter the material 16C of the container 16. Continued penetration of delivery needle 26 into container 16 will thereby result in the flap 16D and the material 16C being pushed aside or otherwise distorted by anti-coring edges 26F to finish forming the passage through the wall of the container 16 while leaving the flap 16D attached to the wall of the container 16.

The above described penetration of the wall of the container 16 and the forming of a hole or passage with an attached flap 16D will be repeated when the delivery needle 26 reaches and penetrates the opposite wall of the container 16, but with the flap 16D being formed on the outer side of the container 16 wall rather than on the inner side of the container.

Continuing with alternate embodiments of a delivery needle 26 as illustrated in FIGS. 2A-2C, it will be apparent from the illustrated examples of alternate embodiments that the basic geometry of the above discussed needle 26, and in particular the configuration of the puncture point or points and various edges, may be configured in a number of ways. It must also be noted that each delivery needle 26 will include at least one air inlet 26A opening into a corresponding one of air passages 18B and 18C, thereby allowing a passage of exterior air into the interior of hollow delivery needle 26 and up needle 26 towards the medication container 16 and, eventually, mouthpiece chamber 12A and the user.

Each delivery needle 26 will further include at least one medication inlet 26M in the region of and opening into the interior of the medication container 16 to allow the medication contained in the medication container 16 to be drawn into the interior of the delivery needle 26 and up the interior of the delivery needle 26, together with the exterior air from air inlets 26A, and into the mouthpiece chamber 12A and to the user.

In the instance of a medication delivery needle 26 as illustrated in FIGS. 2A-2C, the opening formed by puncture plane 26C cutting across the diameter of the medication delivery needle 26 to form the puncture point 26P, the puncture plane 26C, the puncture edges 26E, the cutting edges 26D and the anti-coring edges 26F will comprise an air inlet 26A. A medication delivery needle 26 as illustrated in FIGS. 2A-2C will also include one or more air/medication ports 26G in the length of the medication delivery needle 26 above puncture plane 26C. As will be described further in the following air/medication ports 26G may extend on both the inner and the outer sides of the lower opening of the punctured medication container 16, so that each air/medication port 26G will serve both as a air inlet 26A and a medication inlet 26M.

Figure 3B:
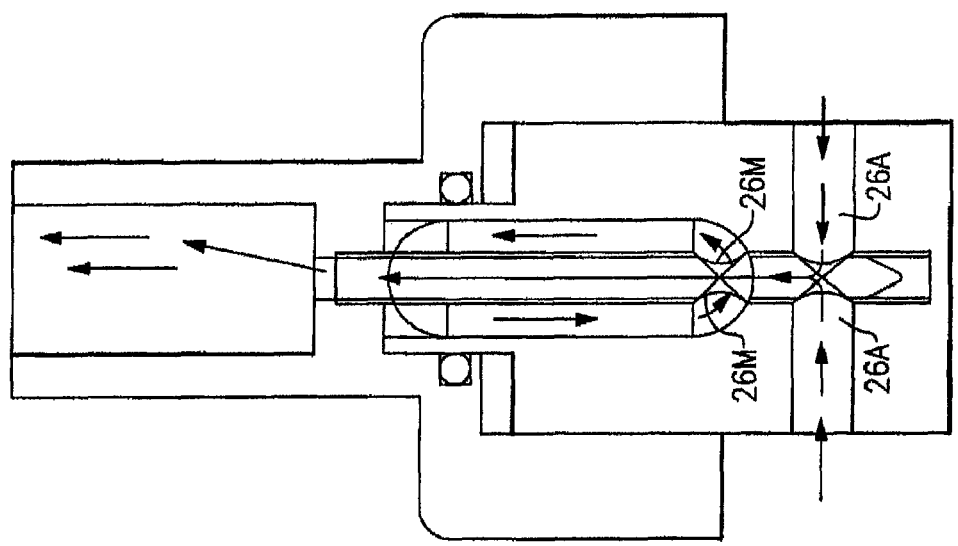
FIGS. 3A-3D are diagrammatic representations of alternate embodiments of a dry medication inhaler.
Figure 3A:
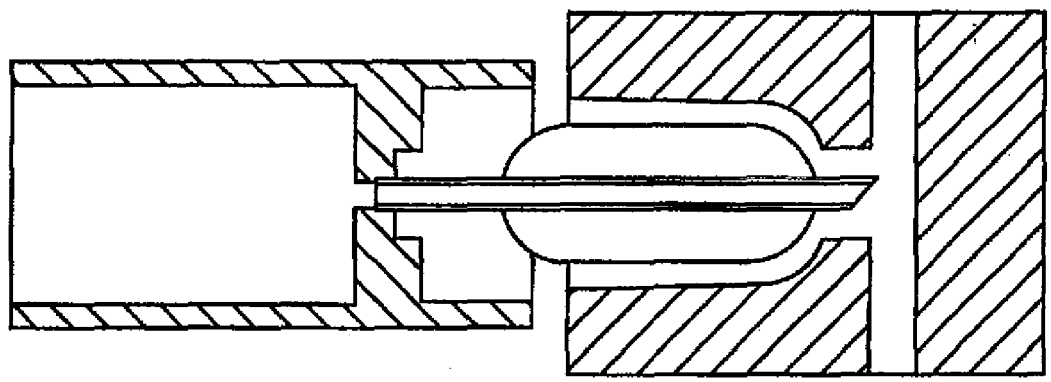
Figure 3D:
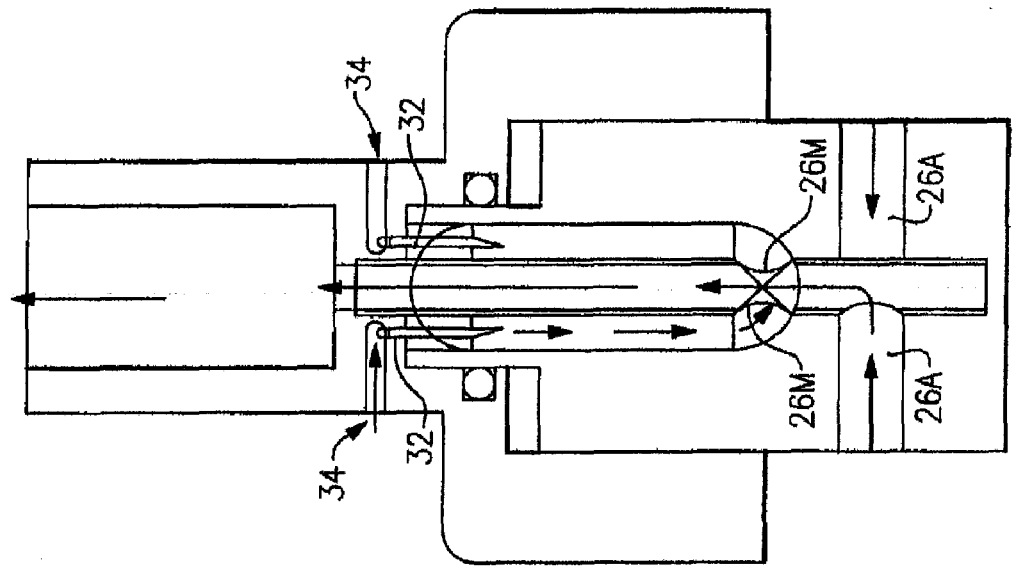
Figure 3C:
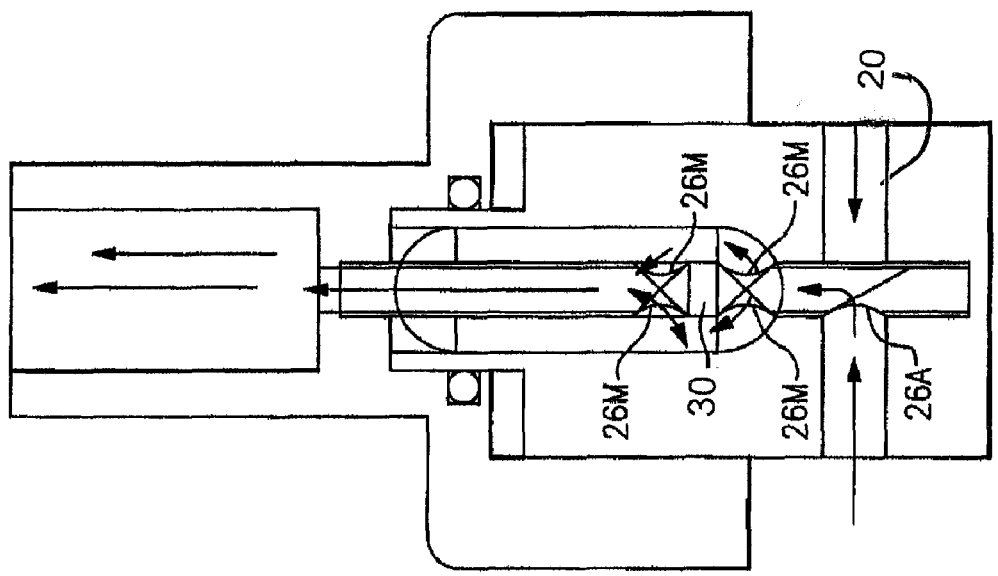

Referring now to FIGS. 3A-3D, FIG. 3A is a view of an assembled inhaler 10 and FIGS. 3B-3D are diagrammatic representations of alternate embodiments of an inhaler 10. FIG. 3B, for example, illustrates an inhaler 10 wherein the delivery needle 26 is provided with a penetrating point 26P.

FIG. 3C shows a delivery needle 26 having two vertically spaced pairs of medication ports 26M separated by a baffle 30 closing the interior bore of the delivery needle 26 between the upper and lower pairs of medication inlets 26M. This design prevents clogging and clumping of the medication within the medication container 16 by forcing air drawn from air passage 20 and into the lower part of the delivery needle 26 to vent into the medication container 16, thereby increasing the efficiency of "scouring" of the medication from the container 16 by providing a greater pressure differential through the container 16, and thus a greater volume of air flow. Depending upon the type and composition of medication in the container 16, this design may also provide a "stirring" of the medication therein before carrying the medication out of the container 16 through the upper pair of medication ports 26M and up through the needle 26 to the mouthpiece chamber 12A, thereby reducing the possibility of "clogging" or trapping of the medication in the container 16 or the flow passages.

FIG. 3D in turn illustrates an embodiment of an inhaler 10 that addresses the same approaches as the embodiment of FIG. 3C, but in a different form. In the embodiment of FIG. 3D, in addition to medication needle 26, which may include one or more air/medication ports 26G, the lower part of mouthpiece 12 that abuts main body 14 and, in particular, container chamber 14C, supports one or more hollow secondary needles 32 that connect with the exterior air through corresponding secondary air passages 34, and that extend into container chamber 16. When mouthpiece 12 and main body 14 are moved into the activated position, secondary needles 32 will penetrate the medication container 16 so that air will be drawn through air passages 32 and secondary needles 34 and into the upper part of the medication container 16 when the user draws on mouthpiece 12. The resulting flow of air into the upper part of the medication container 16 and downwards and out through medication inlets 26M will assist in preventing clogging and clumping of the medication and will assist in carrying the medication out of the medication container 16 and up needle 26 to mouthpiece chamber 12A. It will be understood by those of ordinary skill in the relevant arts that the diameters of secondary needles 32 and needle 26 and of the various air and medication ports and passages must be selected in consideration of the suction that can be comfortable exerted on mouthpiece 12 by a patient, the air flow necessary to move the medication to the patient, and the desired rates and proportions of air and medication flows through the inhaler 10

It will be understood that the inhaler 10 of the present invention, including the mouthpiece 12, the main body 14A, and the medication delivery needle 26, may be constructed of any of a range of materials suitable to their intended purposes, such as glass, metal, plastics or ceramics. It will also be understood that the term "container" used in the above descriptions, such as the medication container 16, is used in the generic and general meaning as a container for medication, rather than in a specific and limiting sense. It will be apparent from the above discussions that a "container" as the term is used herein and in the claims may assume any of a variety of shapes other than the generally oval capsule shown herein for illustrative purposes, such as a blister pack, and that the container may be made of any of a wide range of materials. It must also be understood that the specific shapes, proportions and dimensions of the various elements of an inhaler 10 will be at least in part dependent upon the constitution of the medications to be dispensed. In the case of dry medications, for example, some medications are comprised of pure medication, often comprised of "snowflake"-like particles, while others are comprised of particles of medication attached to particles of a carrier material, all of which may effect the materials and dimensions of a specific design of an inhaler 10.

Figure 5:
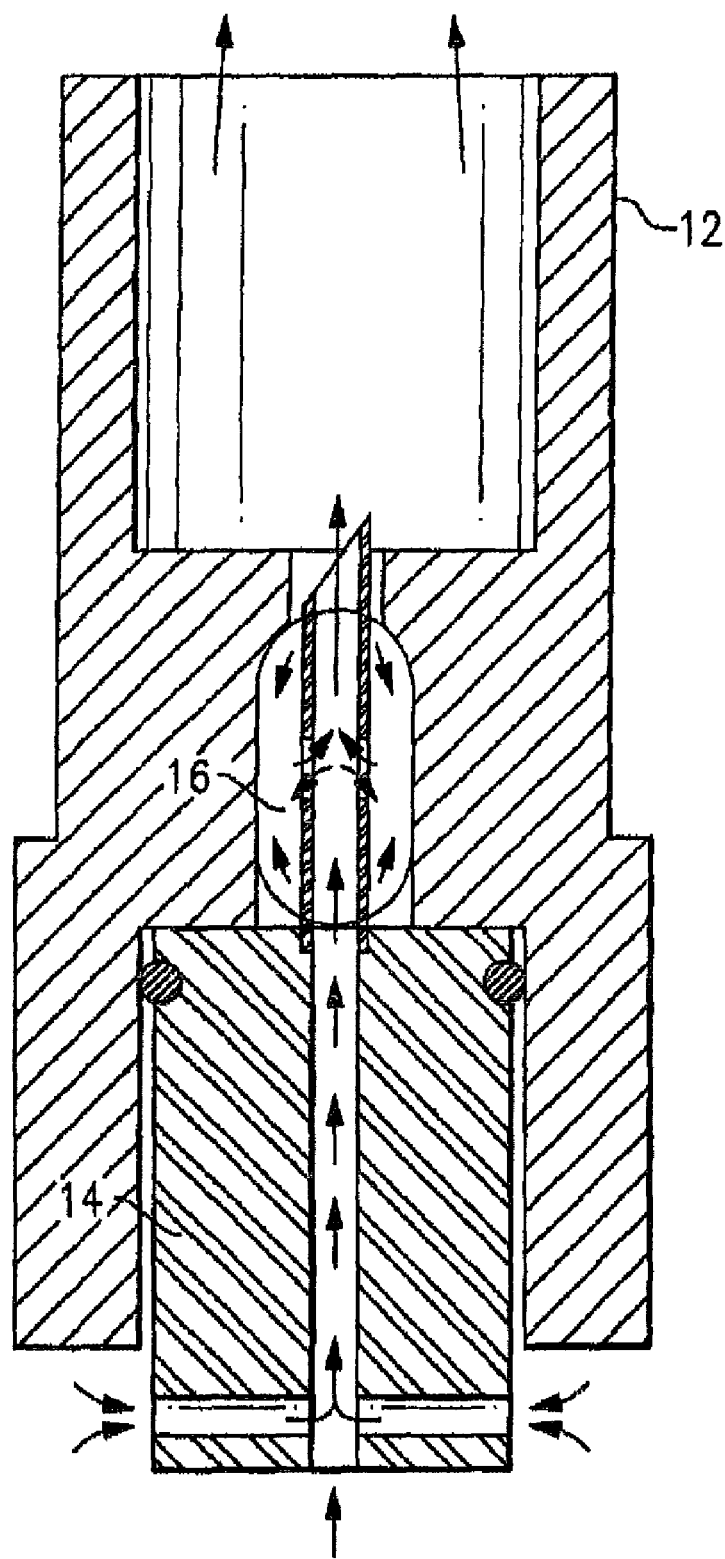
FIG. 5 is a diagrammatic representation of an alternate embodiment of a dry medication inhaler in which the roles of the mouthpiece and body are reversed with respect to the location and operation of the medication delivery needle.

In further examples, of alternate embodiments or features, the delivery needle 26 may extend into mouthpiece chamber 12A, or the entry of needle passage 12C may be surrounded by a cylindrical baffle, to direct the flow of air and medication from needle passage 12C towards the mouthpiece outlet to the user, thereby assisting in preventing clumping and clogging and the deposition of the medication on the inner surfaces of the mouthpiece chamber 12A. The circumference of the lower part of mouthpiece chamber 12A may also include additional air inlets for the same purpose, that is, the creation of air currents to direct the mixture of air and medication as desired. Yet another alternate embodiment is illustrated in FIG. 5, which is a diagrammatic representation of an alternate embodiment of a dry medication inhaler in which the roles of the mouthpiece and body are reversed with respect to the location and operation of the medication delivery needle.

It should also be noted that while an inhaler 10 of the present invention is intended for use with dry medications in the presently preferred implementations, it is possible to use the inhaler of the present invention with, for example, a "dry" medication comprised of a "wet" medication retained in the container in, for example, an air gel or other absorbent or micro-pore material, or semi-solid medications, either of which would be delivered by evaporation or sublimation into the air flowing through the container. In this sense, therefore, the term "dry" medication includes medications that are "wet" but not liquid in the sense of a substance that will flow readily.

In still further examples of possible implementations of the present invention, an inhaler 10 has been described herein above as a single-container single-use device, as a single-container multi-use device, and as a pre-loaded ready-to-use device. In yet other embodiments the inhaler 10 may be implemented as a "multi-shot" device wherein, for example, main body 14 is provided with multiple container chambers 14B that can be selected by, for example, rotating or sliding the main body 14A, or with a single container chamber 14B and a rotary or sliding magazine for loading successive containers 16 into the container chamber 14B.

B. Effects of Container Size on Embodiments

As described briefly above, medication containers 16 may differ significantly in size, that is, length, width and capacity, as well as shape and in the materials from which they are manufactured. Examples of the dimensions of typical capsules are illustrated in FIG. 6C.

Figure 6C:
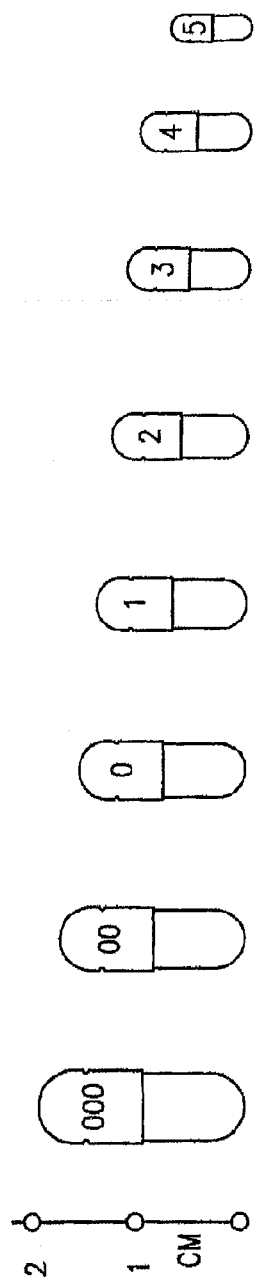
FIG. 6C is a table illustrating capsules of various sizes and capacities.

That is, and as illustrated in FIGS. 6A and 6B, wherein FIG. 6A illustrates a larger capacity capsule and FIG. 6B a smaller capacity capsule, the adaptation of a dry inhaler 10 of the present invention to containers of different capacities, dimensions, and shapes often requires only changes in the internal dimensions of container chamber 14C and a possible change in the diameter of delivery needle 26 so that the diameter of delivery needle 26 is compatible with the diameter of the medication container 16. The external configuration and dimensions of the dry inhaler 10, however, may remain the same for a wide range of embodiments for different container capacities, dimensions and shapes, examples of which are illustrated in FIG. 6C. It should be noted, however, that the external configuration or dimensions of a given embodiment of an inhaler 10 or a portion thereof could be varied to provide, for example, a visual or tactile differentiation between inhalers 10 loaded with different medications or dosages or with medication containers other than capsules.

In this regard, it must be recognized and understood that while the inhaler 10 of the present invention is generally illustrated and described herein in terms of medication containers 16 in the form of gelatin capsules, that other forms of medication containers 16 may be used readily and with equal facility in an inhaler 10 of the present invention. For example, medication containers 16 may be comprised of blister type packages or other forms of molded containers or that, for example, the medication could be formed into a frangible container or pellet, so that the medication effectively forms its own container. In this instance, for example, the container chamber 14B would effectively form the outer encapsulation of the medication container and would retain the medication in both its sold form and in its powdered form after it had been crushed or pierced by the needle.

C. Alternate Needle Configurations

It will be understood, as discussed above, that the dimensions and configuration or shape of a least certain of the inhaler 10 components, such as the diameter and lengths of mouthpiece 12, body 14, container chamber 14B and medication delivery needle 26 will be dictated largely by the number and dimensions of the containers 16 and the requirements to transport the medications from the container to the patent. It will be apparent that other factors dictating or influencing the dimensions and configurations of the inhaler 10 components and assembly will include, for example, the requirements of a patient or other person in loading and using the inhaler 10, and the possible adaptations of the inhaler 10 components and assembly, for example, the automated manufacture and assembly of the components, including the assembly and loading of pre-loaded inhalers 10.

In this regard, it must be understood that the shape, configuration and dimensions of medication delivery needle 26 will have a significant effect on such factors as how the needle 26 penetrates and opens a medication container 16 and how the medication therein is transported from the container 16 to the patient by the air flow through the container 16 and needle 26. For these reasons, therefore, the following will discuss various embodiments and variations in medication delivery needle 26 and other related aspects of an inhaler 10.

Referring first to FIGS. 7A-7D, therein are shown diagrammatic illustrations of an embodiment of a dry inhaler 10 of the present invention and an implementation of medication delivery needle 26 as employed therein. It will be seen from FIGS. 7A-7D that the component parts, configuration and structure of the inhaler 10 represented therein correspond generally to those discussed herein above with regard, for example, to FIGS. 1A-1C, 3A-3C, 4 and 5, and that the shape, configuration and operation of medication delivery needle 26 correspond generally to the medication delivery needle 26 described, for example, in FIGS. 2D-2E.

Figure 7A:
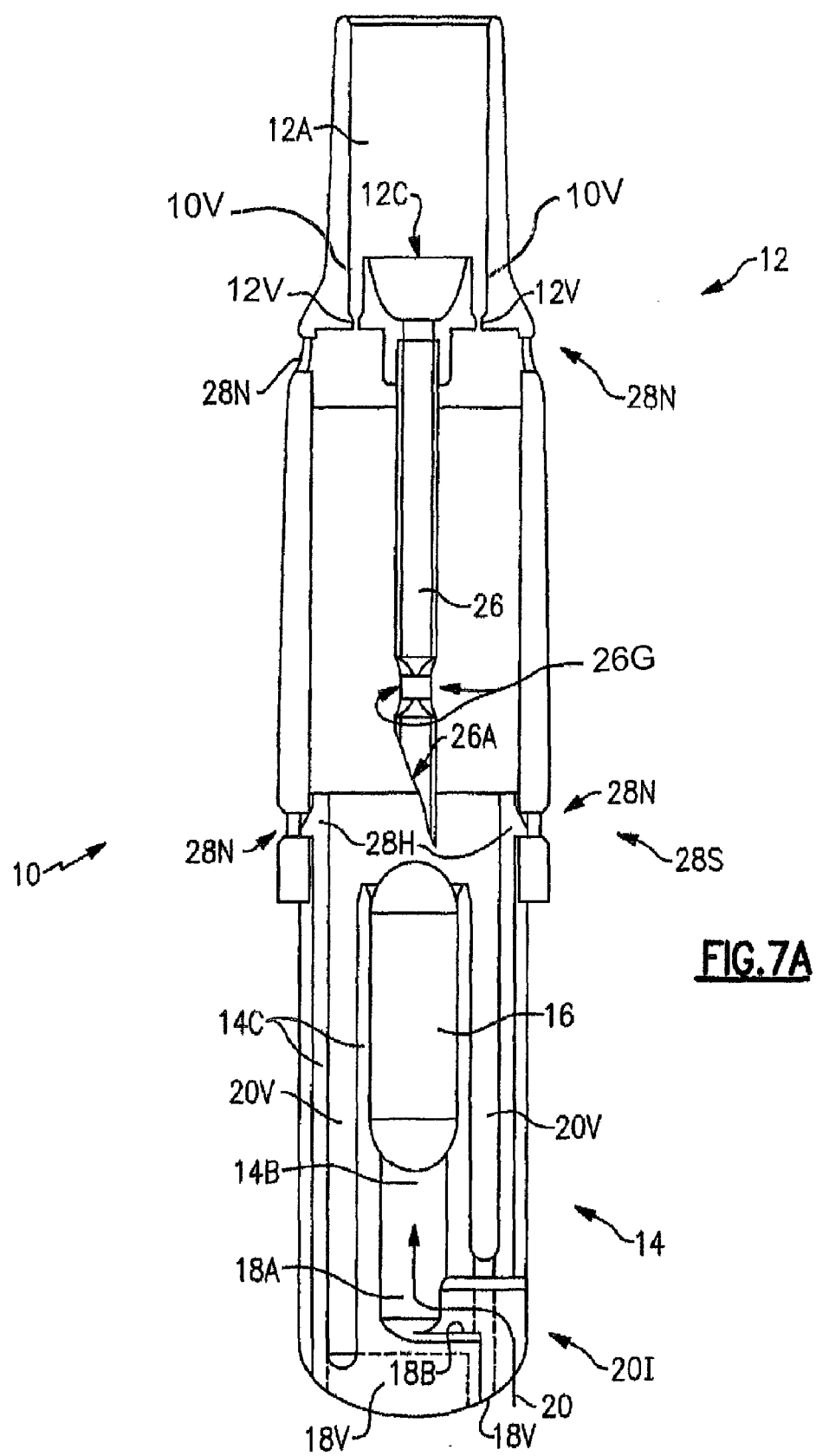
Figure 7B:
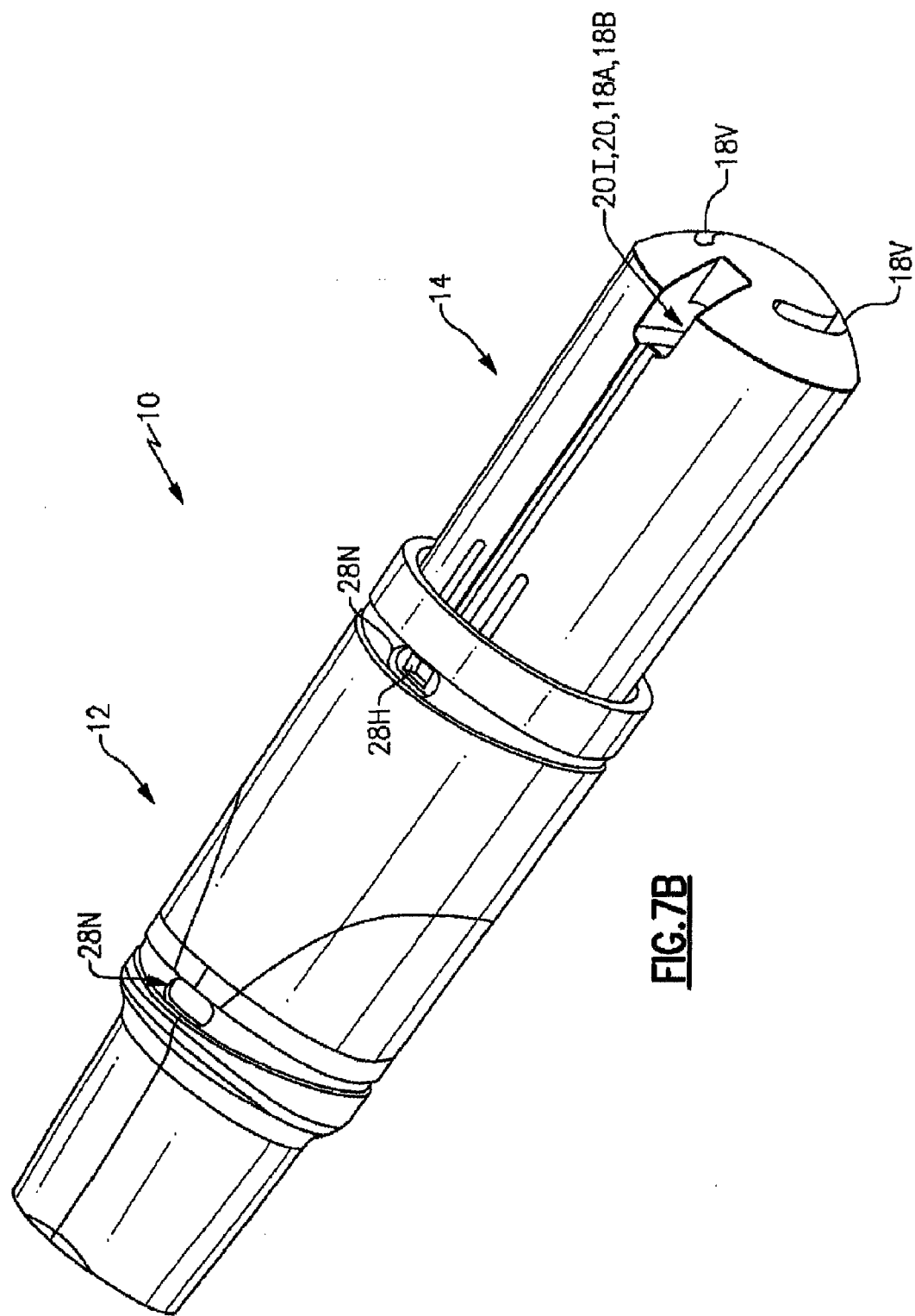

In a typical implementation such as illustrated in FIGS. 7A-7D, for example, needle 26 is approximately 1 inch long and 0.11 inch in diameter with an inner bore diameter of approximately 0.08 to 0.09 inch. There are two air/medication ports 26G located on diametrically opposite sides of the needle 26 and each air/medication port 26G is approximately 0.15 inch long. It will also be noted that when the illustrated inhaler 10 is in the actuated state, that is, mouthpiece 12 and body 14 are pushed together as far as possible and needle 26 has penetrated the container 16 to the maximum extent, as discussed above, the air/medication ports 26G are positioned such that a part of their length is within the container 16 and a part extends outside the container 16. As discussed, air/medication ports 26G thereby function as both air inlets 26A and medication inlets 26M. The configuration is also such as to provide the optimum air flow rate and circulation pattern to carry the medication from the container 16 into the needle 26 and to the patient through needle 26 and mouthpiece 12, as illustrated in FIG. 7A.

It will also be noted that the length of needle 26, and the length of container chamber 14B, are selected so that puncture point 26P does not contact the lower end of container chamber 14B and so that the lower inner side of mouthpiece 12, through which needle 26 passes, does not contact and inadvertently crush the container 16.

In addition, it must be noted that the opening formed by puncture plane 26C cutting across the diameter of the medication delivery needle 26 to form the puncture point 26P, the puncture plane 26C, the puncture edges 26E, the cutting edges 26D and the anti-coring edges 26F will comprise an air inlet 26A that, like the lower portion of the air/medication ports 26G, communicate with lower air passage 20 to receive exterior air. Lastly in this regard, should be noted that in this implementation lower air passage 20, connecting air/medication port 26G and the air inlet 26A to the exterior air, is comprised of a single vertical air passage 18A and a single horizontal air passage 18B connecting with a slot-like air inlet opening 20I.

In addition, body 14 includes one or more bypass vent passages 20V concentrically located in cylindrical wall 14C between container chamber 14B and the outer surface of body 14 and having, in the present embodiment, arc-shaped cross sections. In the illustrated embodiment the lower ends of bypass vent passages 20V connect with the exterior air through a single vent slot 18V while the upper ends of bypass vent passages 20V connect with mouthpiece chamber 12A through bypass vent ports 12V and bypass vent passages 10V. It should be noted that while bypass vent slots 18V and 10V are illustrated in this example as being arc-shaped, any appropriate shape may be used.

A primary function of bypass vent passages 20V is to enhance the flow of air and medication through mouthpiece 12 and to provide an optimum flow of air and medication to a user of the inhaler 10. As was discussed, body 14 includes one or more bypass vent passages 20V located in cylindrical wall 14C surrounding container chamber 14B with the lower ends of vent passages 20V connecting with the exterior air through one or more bypass vent slots 18V. The upper ends of vent passages 20V, in turn, connect with vent ports 12V and vent passages 10V that extend through mouthpiece 12 between the mouthpiece 12 face abutting vent passages 20V in body wall 14C and mouthpiece chamber 12A. Bypass vent passages 20V, vent passages 10V and vent ports 12V thereby form an air flow path from the exterior air and through body 14 and mouthpiece 12 to mouthpiece chamber 12A, bypassing the air and medication powder flow path through needle 26 and the container 16.

First considering the flow of air and medication in mouthpiece chamber 12A in the above embodiment, mouthpiece chamber 12A receives a significant increase in the airflow passage volume compared to the flow passage through container 16 and needle passage 12C, thereby resulting in a drop in flow pressure and velocity as the medication/air flow from container 16 and needle passage 12C enters mouthpiece chamber 12A. The additional flow of air into mouthpiece chamber 12A through bypass vent passages 20V, vent passages 10V, and vent ports 12V, however, assists in maintaining the flow rate per unit volume in mouthpiece chamber 12A by increasing the volume of air flowing into and through mouthpiece chamber 12A, thereby assisting in maintaining the flow pressure and velocity of the combined air flow through mouthpiece chamber 12A.

In addition, it has been found that there is a range of air/mediation flow parameters, such as air flow volume, flow resistance through the inhaler 10, suction applied by the user to cause the flow of air and medication to the user and time for delivery of the medication, that is optimum with regard to user comfort and the efficient delivery of medication to the user. That is, if the flow resistance through the inhaler 10 is too great, the user may not be able to exert sufficient suction or exert suction over a sufficient period of time to draw the medication from the container 16. If, however, the flow resistance is too low, the effect could be akin to "stepping on a step that isn't there," or the user could receive a sudden, excessive surge of powdered medication. Bypass vent passages 20V, however, permit the flow resistance of the inhaler, and thus the suction required of the user, and the volume of air and air and medication flowing to use, and thus the period over which the medication is delivered, to be adjusted to the optimum combination for the users.

It must also be noted in this regard that the flow rate and flow resistance through the inhaler 10 represents the combined flow rates and resistances of the parallel flow paths through vent passages 20V and container 16/needle 26 and that the medication is contained only in the flow though container 16, needle 26 and needle passage 12C. Given a desired inhaler 10 flow rate and resistance, therefore, the rate of delivery of the medication and the period during which the medication is delivered is determined by apportionment of the combined flow rate through the inhaler 10 between the two flow paths, which thereby determines the flow rates and resistances through the two paths.

In a presently preferred implementation of an inhaler 10 using a needle 26 and having bypass vents, for example, the presently preferred ratio of air-bypass flow rate to needle flow rate is approximately of 75% to 25%, respectively, with a pressure drop through the inhaler 10 of approximately 0.3 PSI at 28 L/min or 4 KPa at 25 L/min, which provides a very comfortable inhalation resistance for patients. The possible range of ratios of air-bypass flow rates to needle flow rates could, however and for example, be as high as 0% through the bypass and 100% through the needle, which would increase the airflow resistance to the patient but would also increase the medication flow rate and delivered volume of medication, increase patient resistance, but also increase emitted dose. In theory, the ratio of air-bypass flow to needle flow could be from between 0%:100% bypass to needle flow ratio to 80%: 20% bypass to needle flow ratio. It has been found by experiment, however, that bypass/needle flow ratios of less than 20% of the flow through the needle results in dosage deliveries that are flow rate dependent while bypass/needle flow ratios of greater than 20% through the needle tends to provide dosage deliveries that are significantly less dependent on the flow rates.

Bypass vent passages 20V assist in the extraction of medication from container 16 and through needle 26 and mouthpiece 12 by increasing the airflow through mouthpiece 12 to, in turn, create a suction effect to draw increase air through the container 16 and needle 26.

Referring next to FIGS. 8A-8D, therein are illustrated an alternate embodiment of a medication delivery needle 26, designated as a pyramidal point medication delivery needle 36. As shown, a pyramidal delivery needle 36 is comprised of a hollow tubular body 36T having a lower end terminated and closed by a pyramidal puncture point 36P and at least one air/medication port 36M. As shown in FIG. 8B, air/medication port or ports 36M are located along the body 36T or needle 36 so that when the illustrated inhaler 10 is in the actuated state, that is, mouthpiece 12 and body 14 are pushed together so that needle 36 has penetrated the container 16 to the maximum extent, air/medication port or ports 36M are located partly within the container 16 and partly within and correcting to lower air passage 20. For example, when the inhaler 10 is fully actuated the port or ports 36M may be located with approximately 9/10ths of the port or ports within the container 16 and approximately 1/10th communicating with lower air passage 20. It will, therefore, be apparent that in a pyramidal needle 36, the pyramidal puncture port 36P closes the end of tubular body 36T so that the needle 36 does not include an air inlet 26A at the lower end of the needle 36 and so that the air/medication port or ports 36M of the needle 36 function as both air inlets 26A and medication inlets 26M of the needle 36 in a manner analogous to air/medication ports 26G of needle 26.

As illustrated in FIGS. 8A-8D, pyramidal puncture point 36P may assume the form of, for example, a three or four sided pyramid with the tip of the pyramid, which forms the point puncturing the container 16 when the inhaler 10 is actuated, being located on the centerline of the needle 36 and thereby on the centerline of the container 16. Comparison with the puncture point 26P of a needle 26 as shown, for example, in FIG. 2F, will show that rather than cutting a single large flap 16D of container material 16C when penetrating the wall of a container 16, as in the case of a needle 26, a pyramidal puncture point 36P will form openings bounded by three or four small flaps through the walls of a container 16, depending on the number of faces of the pyramid.

It is anticipated that the use of a pyramidal puncture port will reduce the probability of one or more broken off container wall material 16C flaps 16D blocking the transport of medication and air from the container 16 to the patient being taken up by the patient together with the medication. It will be recognized, however, that the choice of a needle 26 or a needle 36 for a given inhaler 10 will often be determined by the dimensions and material or materials comprising the container 16, and that each design of needle will be advantageous in certain circumstances.

Lastly in this regard, it will be noted that a pyramidal needle 36 is illustrated in FIGS. 8C and 8D as being comprised of hollow, tubular body 36T and a separate pyramidal point 36P that is mounted into the end of the body 36T. It will be recognized, however, that a pyramidal needle 36 may be manufactured in a number of alternate ways, including as a pyramidal needle 36 wherein the body 36T and the pyramidal point 36P are formed as a single component. For example, a needle 36 may be manufactured by an injection molding process or by a plating molding process wherein a material is plated or otherwise deposited on a mold form. In other example, a single part needle 36 may be fabricated by a process wherein the needle 36 is initially manufactured as a hollow tube with the lower end of the tube subsequently being "notched" into three or four "petals" or triangles that are then crimped or squeezed together to form the pyramidal point, at the same time closing the end of the hollow tube forming the body 36T of the pyramidal needle 36.

Referring to FIG. 8E, therein is illustrated a yet further embodiment, of an inhaler 10 with a yet further alternate embodiment of a medication delivery needle 26, designated as a double medication delivery needle 26Z comprised of an upper delivery needle 26X and a lower delivery needle 26Y. As illustrated therein, the lower end of needle passage 12C, that is, the end of needle passage 12C ending at body chamber 12B terminates in upper delivery needle 26X wherein upper delivery needle 26X extends into body chamber 12B by a distance sufficient to penetrate into the upper end of a container 16 when the inhaler 10 is activated as described herein above. Upper needle 26X may assume any of the needle forms described herein above, such as those illustrated in FIGS. 1B and 8A, and will include an air and medication passage extending through upper needle 26X to the lower end of upper needle 26X to terminate in one or more inlets 26M located at the lower end of the upper needle 26X. Upper needle 26X need not necessarily include one or more air/medication ports 26G, however, but may do so.

As also illustrated, the lower end of mouthpiece 12 further includes a container support/guide 12D that extends into upper chamber 12B around upper needle 26X to receive, guide and support the upper end of the container 16 during activation of the inhaler 10, when mouthpiece 12 and body 14 are axially telescoped so that double needle 26Z penetrates the ends of the container 16. In a presently preferred embodiment as illustrated in FIG. 8E, the lower surface of container support/guide 12D forms a concave surface shaped at least generally to the shape of the end of the container 16. Container support/guide 12D, and in particular the outer rim portion of container support/guide 12D, extends into upper chamber 12B by a distance sufficient to support and guide the container 16 during the inhaler 10 activation operation, and the length and shape of container support/guide 12D is such as not to interfere with body 14 when the inhaler 10 is activated. In this regard, it will be noted that in the illustrated embodiment the outer diameter of container support/guide 12D is sufficiently large to enclose at least a significant portion of the upper end of the container 16. However, the outer diameter of container support/guide 12D is less than the inner diameter of upper chamber 12B in the illustrated embodiment, to allow a corresponding portion of body 14 to extend into and interlock with mouthpiece 12 in this space, in a manner similar to that illustrated with respect to FIG. 1A. In other embodiments, however, container support/guide 12D may extend the full width of upper chamber 12D and the length of container support/guide 12D may be such that there will not be interference between mouthpiece 12 an body 14 when the inhaler 10 is activated.

Lower needle 26Y, in turn, terminates lower air passages 18A and 20 and extends upward into body chamber 12A by a distance sufficient to penetrate into the lower end of container 16 when the inhaler 10 is activated as described herein above. Again, lower needle 26Y may assume any of the needle forms described herein above, such as those illustrated in FIGS. 1B and 8A, and will include an air and medication passage extending through lower needle 26Y to the upper end of lower needle 26Y to terminate in one or more outlets 26M located at the upper end of lower needle 26Y. Also again, lower needle 26Y need not necessarily include one or more air/medication ports 26G, but may do so.

Lastly, it will be recognized that when an inhaler 10 as illustrated in FIG. 8E is activated by axially telescoping the mouthpiece 12 and body 14, upper and lower needles 26X and 26Y will pierce the enclosed container 16 to form generally the same air/medication passage through the container 16 and to the patient as has been described elsewhere herein above with respect to other forms of the needle 26/36. In this regard, it will be recognized that the implementation illustrated in FIG. 8E differs essentially in that the middle portion of the air/medication passage through container 16 is comprised of container 16 itself, rather than of the body of the needle 26/36. It will also be recognized that the implementation shown in FIG. 8E allows a simpler needle 26Z because the needle is comprised of two short needles rather than one longer and thus mechanically weaker needle. In addition, the use of two shorter needles reduces the requirements for alignment of the needle or needles because each of needles 26X and 26Y needs only to be generally aligned with the axis of the container 16 and chambers 14a and 14B. In implementations using a single longer needle, however, the needle must be aligned along the entire length of chambers 14A and 14B and container 16 so as to penetrate the lower end of the container 16 and enter the lower air passage.

D. Alternate Embodiments

Windowed Inhalers 10

Referring to FIGS. 9A and 9B, therein are illustrated an embodiment of an inhaler 10 having container windows 38A and 38B in, respectively, the side walls of mouthpiece 12 and body 14, to allow visual inspection of the existence and state of a medication container 16 residing in the chamber 14B of body 14. The mouthpiece 12 and body 14 may have matching pairs of windows 38A and 38B located on diametrically opposite one another in mouthpiece 12 and body 14, or may have a single pair of windows 38A and 38B respectively located only on one side of the mouthpiece 12 and body 14. The latter embodiment may require that the body 14 or the body 14 and mouthpiece 12 be comprised of, for example, a transparent or translucent material, to allow sufficient light to enter the chamber 14B to illuminate a container 16 therein, or that the body 14 and mouthpiece 12 have a light port located opposite the windows 38A and 38B for the same purpose.

It will be noted that in the embodiment specifically illustrated in FIGS. 9A and 9B the container widow or windows 38B in body 14 are located directly adjacent chamber 14B and are of a length sufficient to allow a clear view of a container 16 in the chamber 14B. It will also be noted that in this embodiment the window or windows 38A in mouthpiece 12 are located so as to be directly adjacent the window or windows 38B when the inhaler 10 is actuated, that is, when the body 14 has entered mouthpiece 12 to an extent that the medication is released to the patient. This arrangement will allow visual inspection of the actuated inhaler 10 to provide an indication of whether there was a medication container 16 in the inhaler 10 and whether or to what extent the medication therein has been delivered to the patient.

It may also be desirable to allow inspection of, for example, a pre-loaded but not yet actuated inhaler 10, such as an inhaler 10 that has been stored in the pre-loaded state, which would require providing a view of the chamber 14B while the mouthpiece 12 and body 14 were in the non-actuated position. This may be accomplished, for example, by designing the body 14 and mouthpiece 12 so that at least a portion of the window 38B and chamber 14B extend outside the mouthpiece 12 when the inhaler 10 is in the non-actuated position. In other embodiments, such as embodiments wherein chamber 14B is enclosed within mouthpiece 12 in the assembled but non-actuated position, the window 38A in mouthpiece 12 may be extended to overlap the window 38B in body 14 when body 14 is in the non-actuated position. Alternately, the mouthpiece 12 may be provided with two axially spaced windows 38A, one located to correspond with window 38B when body 14 is in the non-actuated position and one located to correspond with window 38B when body 14 is in the actuated position.

It should also be noted that windows 38A and 38B comprise a passage through the walls of mouthpiece 12 and body 14 and into the chamber 14B, which may raise questions of preventing loss of the medication through the windows 38B and 38A or of an unwanted flow of air through the windows and into the chamber 14B. This issue, however, may be addressed in a number of ways, such as sealing the window 38B through the wall of the chamber 14B with a transparent or translucent "window pane", using a container 16 of dimensions and material suitable to provide and preserve the sealing of the chamber 14B, or manufacturing the body 14 of a transparent or translucent material that will pass light while providing a sealed chamber 14B.

E. Alternate Embodiments

Multiple Dose Inhalers 10

As discussed elsewhere herein, an inhaler 10 may also be designed to contain and deliver multiple medication dosages, thereby including a mechanism or structure to hold multiple medication containers and to allow the selection and actuation of individual medication containers. The mechanism for holding and selecting among multiple medication containers may, for example, assume the form of a magazine or clip inserted into the body 14, such as used to load cartridges into firearms, or the body 14 may itself contain multiple chambers 14B, similar to the chambers in a revolver cylinder. In this case of a magazine or clip mechanism the entire clip or magazine could be provided with an overpack to provide the necessary shelf life, or the individual containers could be contained in individual overpacks. In the case of a revolver cylinder arrangement with multiple chambers 14B it would be possible to provide, each medication container 16 with an individual overpack, or the body 14 with the medication containers 16 therein could be provided with an overpack. It will be recognized, in this regard, that those implementations of a clip or magazine or a body 14 with an overall overpack, as opposed to individual overpacks for the individual containers 16, it would be necessary to use all of the dosages within the "opened package" shelf life.

Figure 10A:
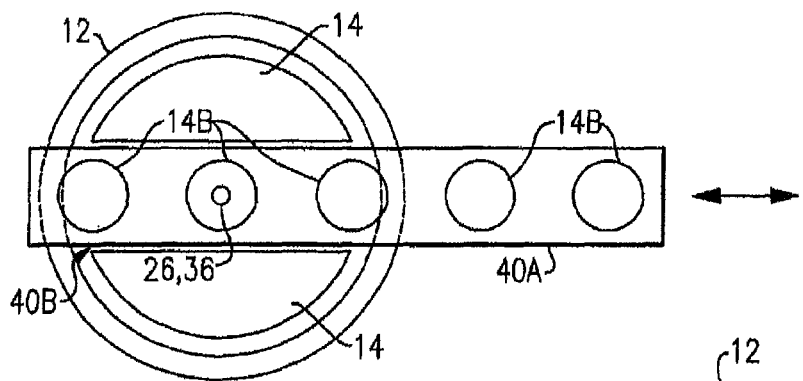
FIG. 10A is a diagrammatic end view illustration of an inhaler accepting a linear magazine containing multiple chambers and containers.

Examples of such embodiments of an inhaler 10 are illustrated in FIGS. 10A through 10D wherein FIG. 10A is a diagrammatic end view illustration of an inhaler 10 accepting a linear clip or magazine 40A containing multiple chambers 14B and corresponding containers 16. As shown therein, mouthpiece 12 and body 14 include a magazine slot 40B axially traversing mouthpiece 12 and body 14 at the axial location occupied by the chamber 14B in the previously described embodiments of an inhaler 10. That is, so that the needle 26/36 is short of the container 16 in the chamber 14B currently aligned with the needle 26/36 when the body 14 is in the non-actuated position with respect to mouthpiece 12 and so that the needle 26/36 will penetrate the container 16 when body 14 is moved to the actuated position with respect to the mouthpiece 12. As will be apparent from FIG. 10A, individual containers 16 may be selected and used in any order by sliding the magazine 40A along magazine slot 40B until the desired chamber 14B and container 16 are axially aligned with the needle 26/36.

Figure 10B:
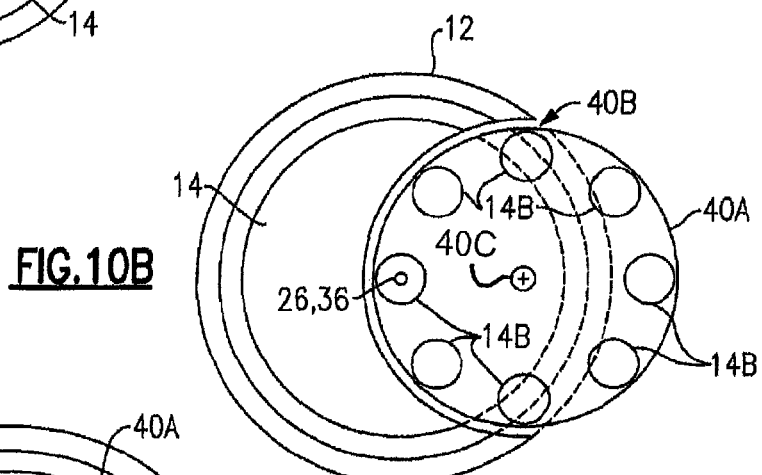
FIG. 10B is a diagrammatic end view illustration of an inhaler accepting a rotary magazine having multiple chambers and containers.

FIG. 10B is a diagrammatic end view illustration of an inhaler 10 generally similar to that of FIG. 10A except that magazine 40A is formed into a circular structure rotating about a longitudinal axis 40C, or axle, located, for example, one an outer rim of body 14 and magazine a lot 40B is correspondingly shaped to accept and support the magazine 40A. In this embodiment, therefore, the magazine 40A is rotated rather than linearly slid to bring the individual chambers 14B and the individual containers 16 therein into axial alignment with the needle 26/36, thereby comprising a revolver cylinder type mechanism.

Figure 10C:
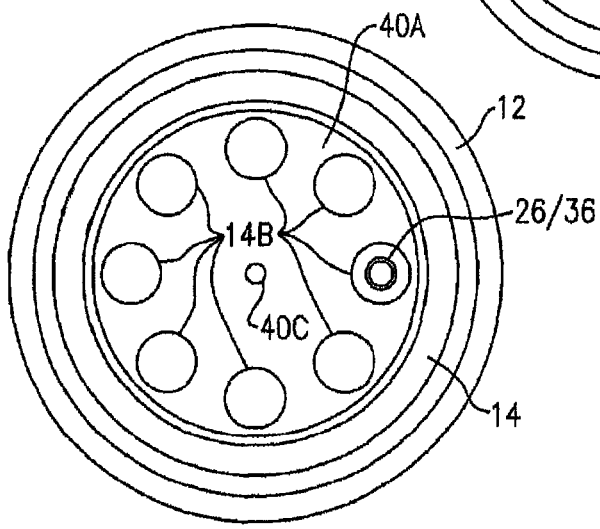
FIG. 10C is a diagrammatic end view illustration of an inhaler having a cylindrical magazine having multiple chambers and containers.

FIG. 10C is a diagrammatic end view illustration of an inhaler 10 having a cylinder-like magazine 40A wherein the magazine 40A rotates about an axis 40C that is coaxial with the central axis of the body 14 and mouthpiece 12 so that the chambers 14B and containers 16 therein rotate about the outer rim of the body 14. In this implementation, the needle 26/36 and air passages described herein above are offset toward the outer circumference of the body 14 and mouthpiece 12 so that the individual chambers 14B and the containers 16 therein are brought into alignment with the needle 26/36 by rotation of the magazine 40A about the centrally located axis 40C. It will be noted that in the implementation the air/medication passage to and through mouthpiece 12 will typically be directed or bent away from the periphery of the body 14/mouthpiece 12 assembly to align generally with the central axis of the mouthpiece 12 to thereby pass to the patient along the central axis of the mouthpiece 12.

Figure 10D:
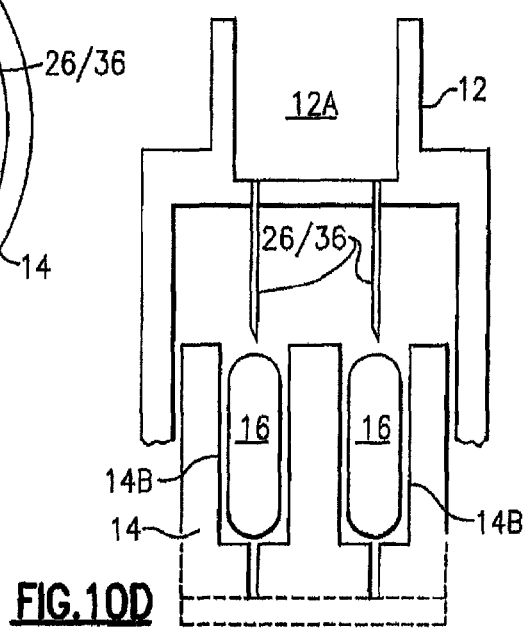
FIG. 10D is a diagrammatic side view illustration of a multiple medication inhaler.

Lastly, FIG. 10D is a diagrammatic side view illustration of a multiple medication inhaler 10 capable of simultaneously delivering a plurality dosages of medications to a patient in a single actuation wherein the medications in the chambers 14B may each be different from one another, or wherein two or more chambers 14B may contain the same medication. It will also be apparent that not all of the chambers 14B must contain medication at a given time and for a given actuation, but it may be preferable to "blank off" the unused chambers 14B to control the air flow through the unused chambers 14B, such as by "dummy" containers 16 or by plugs inserted into the unused chambers 14B.

As illustrated therein, body 14 contains a plurality of container chambers 14B arrange in any manner to accommodate the desired number of chambers 14B within the body 14. The illustrated example includes two chambers 14B arranged in parallel, but it will be recognized that other embodiments may include a larger number of chambers 14B arranged, for example, in a triangular pattern or a circle. As also shown, each container chamber 14B may have an individual air passage 18 for drawing outside air into and through the chamber 14B or wherein, in other embodiments, the air passages 18 of the chambers 14B may be joined into a single air passage 18 serving all of the chambers 14B. The mouthpiece 12 of the multiple medication inhaler 10, in turn, will include a corresponding plurality of needles 26/36 and air/medication passages connecting the chambers 14B with the mouthpiece chamber 12A.

As may be seen from FIG. 10D, therefore, actuation of multiple medication inhaler 10 will result in the simultaneous opening of the containers 16 residing in the chambers 14B so that the patient will then concurrently receive medication from each of the containers 16.

F. Alternate Embodiments

Detent Mechanisms

As discussed herein above, an inhaler 10 of the present invention may include a detect mechanism 28 to hold mouthpiece 12 and body 14 in the "open" position until it is desired to activate the inhaler 10, thereby, for example, allowing the inhaler 10 to be pre-loaded and stored for subsequent use or to be handled safely after loading. Referring lastly to the detent mechanisms 28S of the illustrated embodiment, it will be seen in FIGS. 6A-6C that the detent mechanisms 28S are embodied in a resiliently biased tooth and notch structure that includes opposing paired resiliently biased detent hooks 28H that engage with opposing paired detent notches 28N at two locations along mouthpiece 12. As shown in FIGS. 6A and 6B, one pair of detent notches 28N is located at the position corresponding to detent hooks 28H when the inhaler 10 is in the stored state, that is, when the inhaler 10 is loaded with a container 16 and assembled, but not yet activated, and retains body 14 in the stored position with respect to mouthpiece 12. The second pair of detent notches 28N is located at the position corresponding to the location of detent hooks 28H when the inhaler 10 is in the activated state, that is, when body 14 has been moved into mouthpiece 12 so that needle 26/36 pierces the container 16 to provide access to the medication therein, and retains mouthpiece 12 and body 14 in the activated state.

It must also be recognized with respect to detent mechanisms 28S, however, that any of a wide range of detent types and arrangements are well known in the arts and may be used in place of that illustrated herein. For example, detent mechanism 28S may be comprised of a bayonet type locking mechanism operating between mouthpiece 12 and body 14. In a further example, detent mechanism 28S may be comprised of a thread mechanism wherein matching and engaging portions of mouthpiece 12 and body 14 are correspondingly and engagingly threaded so that rotation of one with respect to the other will draw mouthpiece 12 and body 14 into the activated state.

G. Alternate and Preferred Embodiments

Air and Powder Flow in an Inhaler 10 and Alternate Needle 26/36 Embodiments

The above descriptions have described and discussed various elements and combinations of elements comprising possible exemplary embodiments of an inhaler 10 of the present invention. The following will now describe and discuss various elements of the design of an inhaler 10 with regard to test results obtained from various configurations of those elements. The following will also discuss and describe the optimization of the flow of air and powdered medication through an inhaler 10 for various configurations of elements, and certain presently preferred combinations of those elements and the resulting presently preferred embodiments of an inhaler 10.

As will be noted from the following descriptions of presently preferred embodiments of inhalers 10, all of the presently preferred embodiments use the medication delivery needle described herein above as a pyramidal point medication delivery needle 36. As described previously with respect to FIGS. 8A-8D, a pyramidal delivery needle 36 is comprised of a hollow tubular body 36T having a lower end terminated and closed by a pyramidal puncture point 36P and one or more air/medication port or ports 36M located along the body 36T of needle 36. Air/medication ports 36M are located along the length of the needle 36 so that when the illustrated inhaler 10 is in the actuated state, that is, mouthpiece 12 and body 14 are pushed together so that needle 36 has penetrated the container 16 to the maximum extent, air/medication port or ports 36M are located partly within the container 16 and partly within and connecting to lower air passage 20. For example, when the inhaler 10 is fully actuated, the port or ports 36M may be located with approximately 9/10ths of the port or ports within the container 16 and approximately 1/10th communicating with lower air passage 20. In this embodiment, therefore, and because pyramidal puncture point 36P closes the end of tubular body 36T, the needle 36 does not have an air inlet 26A at the lower end of the needle 36 and the air/medication port or ports 36M of the needle 36 perform the functions of air inlets 26A and medication inlets 26M of a needle 26 as described above.

As also described previously, pyramidal puncture point 36P typically have the form of a four sided pyramid with the tip of the pyramid, which forms the point puncturing the container 16 when the inhaler 10 is actuated, being located on the centerline of the needle 36 and thereby on the centerline of the container 16. As described above, a pyramidal puncture point 36P will form openings through the walls of a container 16 that are bounded by three or four small flaps 16D, depending on the number of faces of the pyramid.

The presently preferred embodiments of an inhaler 10 further include one or more bypass vent passages 20V as described with reference, for example, to FIG. 7C, to enhance the flow of air and medication through mouthpiece 12 and to provide an optimum flow of air and medication to a user of the inhaler 10. As was discussed, body 14 includes one or more bypass vent passages 20V located in cylindrical wall 14C surrounding container chamber 14B, with the lower ends of vent passages 20V connecting with the exterior air through one or more bypass vent slots 18V. The upper ends of vent passages 20V, in turn, connect with vent ports 12V, and vent passages 10V that extend through mouthpiece 12, between the mouthpiece 12 face abutting vent passages 20V in body wall 14C and mouthpiece chamber 12A. Bypass vent passages 20V, vent passages 10V, and vent ports 12V thereby form an air flow path from the exterior air, and through body 14 and mouthpiece 12, to mouthpiece chamber 12A, and bypassing the air and medication powder flow path through needle 36 and container 16.

First considering the flow of air and medication in mouthpiece chamber 12A in the above embodiments, mouthpiece chamber 12A represents a significant increase in the airflow passage volume compared to the flow passage through container 16 and needle passage 12C, thereby resulting in a drop in flow pressure and velocity as the medication/air flow from container 16 and needle passage 12C enters mouthpiece chamber 12A. The additional flow of air into mouthpiece chamber 12A through bypass vent passages 20V, vent passages 10V and vent ports 12V, however, assists in maintaining the flow rate per unit volume in mouthpiece chamber 12A by increasing the volume of air flowing into and through mouthpiece chamber 12A, thereby assisting in maintaining the flow pressure and velocity of the combined air flow through mouthpiece chamber 12A.

In addition, it has been found that there is a range of air/mediation flow parameters, such as air flow volume, flow resistance through the inhaler 10, suction applied by the user to cause the flow of air and medication to the user and time for delivery of the medication, that is optimum with regard to user comfort and the efficient delivery of medication to the user. That is, if the flow resistance through the inhaler 10 is too great, the user may not be able to exert sufficient suction or suction over a sufficient period to draw the medication from the container 16. If, however, the flow resistance is too low, the effect could be akin to "stepping on a step that isn't there" or the user could receive a sudden, excessive surge of powdered medication. Bypass vent passages 20V, however, permit the flow resistance of the inhaler, and thus the suction required of the user, and the volume of air and air and medication flowing to use, and thus the period over which the medication is delivered, to be adjusted to the optimum combination for the users.

It must also be noted in this regard that the flow rate and flow resistance through the inhaler 10 represents the combined flow rates and resistances of the parallel flow paths through vent passages 20V and container 16/needle 36 and that the medication is contained only in the flow though container 16, needle 36 and needle passage 12C. Given a desired inhaler 10 flow rate and resistance, therefore, the rate of delivery of the medication and the period during which the medication is delivered is determined by apportionment of the combined flow rate through the inhaler 10 between the two flow paths, which thereby determines the flow rates and resistances through the two paths.

In a presently preferred implementation of an inhaler 10 using a needle 36 and having bypass vents, for example, the presently preferred ratio of air-bypass flow rate to needle flow rate is approximately of 75% to 25%, respectively, with a pressure drop through the inhaler 10 of approximately 0.3 PSI at 28 L/min or 4 KPa at 25 L/min, which provides a very comfortable inhalation resistance for patients. The possible range of ratios of air-bypass flow rates to needle flow rates could, however and for example, be as high as 0% through the bypass and 100% through the needle, which would increase the airflow resistance to the patient by would also increase the medication flow rate and delivered volume of medication, increase patient resistance, but also increase emitted dose. In theory, the ratio of air-bypass flow to need flow could be between from 0%:100% bypass to needle flow ratio to 80%:20% bypass to needle flow ratio. It has been found by experiment, however, that bypass/needle flow ratios of less than 20% of the flow through the needle results in dosage deliveries that are flow rate dependent, while bypass/needle flow ratios of greater than 20% through the needle tends to provide dosage deliveries that are significantly less dependent on the flow rates.

Having considered the elements common to a range of presently preferred embodiments of an inhaler 10, that is, the use of a pyramidally pointed needle 36 and bypass vent passages 20V, the following will next consider yet other structural features and alternatives that may appear in one or more presently preferred embodiments of an inhaler 10 with reference to FIGS. 11A-11C, 12-17, and 18A-18D. The following will also describe the results of tests performed with various needle 36 implementations and variations.

Figure 11A:
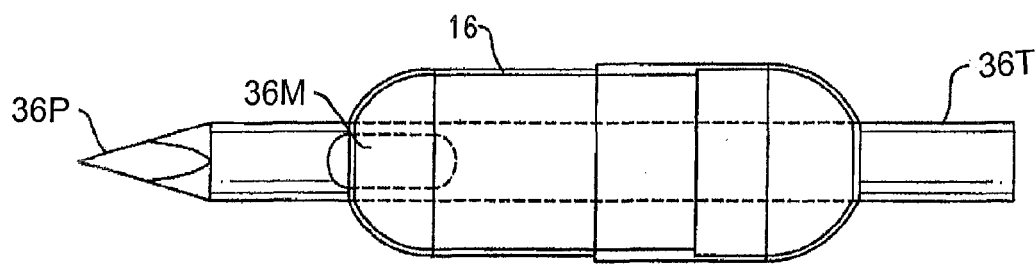
FIG. 11A is a diagrammatic illustration of a basic pyramidal pointed medication delivery needle.
Figure 11B:
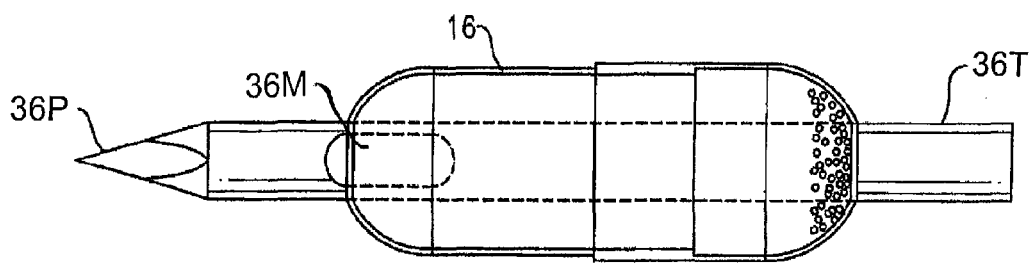
FIG. 11B is an illustration of the impaction and trapping of medication powder in a "dead zone" of a basic needle configuration.

First considering the operation of a basic pyramidal delivery needle 36, FIG. 11A illustrates a pyramidal needle 36 comprised of a hollow tubular body 36T terminated by a pyramidal puncture point 36P and having two air/medication ports 36M located on opposite sides of the body 36T. As shown, air/medication ports 36M are located along body 36T of the needle 36 so that after the needle 36 has fully penetrated the container 16 approximately 9/10ths of the areas of air/medication ports 36M are within the container 16 and approximately 1/10th of the areas of air/medication ports 36M communicate with lower air passage 20. Experiments have found that the basic pyramidal delivery needle 36 as illustrated in FIG. 11A provides excellent air/powder circulation within the container 16, causing good de-agglomeration of the medication particles by operation of vortex shearing and particle-to-particle and particle-to-needle collisions. The basic needle 36 delivered approximately 71% of the powdered medication contained in the container 16 within approximately 750 ms, occasionally leaving behind a small amount of impacted medication powder at a point in the container 16 directly around the area of the needle 36 entry opening into the container 16, as illustrated in FIG. 11B. The average emitted dose of the Irvine needle was around 71-77%.

Figure 11C:
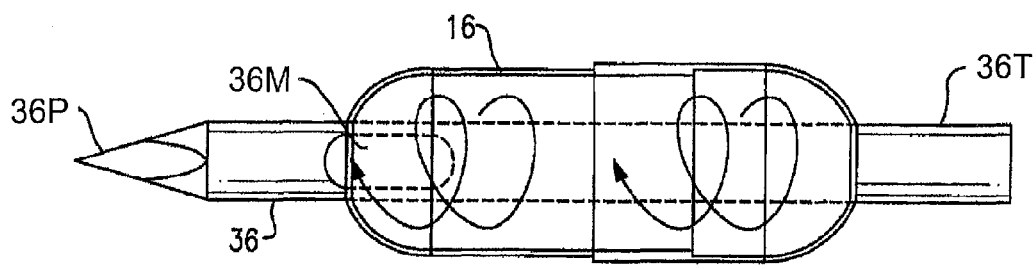
FIG. 11C is an illustration of the formation of vortices in the air and powder flow in a basic needle configuration.

The circulation of air and powdered medication within the container 16 is apparently is caused and driven by a rotational vortex that forms above one of the pair of opposing air/medication ports 36M side of the cross hole in the needle, as illustrated in FIG. 11C. Present evidence indicates that because of variations in the initial puncturing of the container 16, one air/medication port 36M typically has more area exposed to the outside of the capsule 16, that is, communicates with lower air passage 20, while the opposite air/medication port 36M has more area exposed within the capsule. The resulting imbalance in pressures at the air/mediation ports 36M results in one air/medication port 36M becoming an inlet vent from needle 36 and into the container 16 and the other air/medication port 36M becoming an outlet vent from the container 16 and into the interior of the needle 36. The air/medication port 36M functioning as an outlet vent drains the container 16 of powder by forming a stable rotational vortex above its outlet vent air/medication port 36M as illustrated in FIG. 11C. This vortex also induces other sympathetic, stable, vortices within the rest of the container 16. As is typical with free vortices, radial variation of vorticity causes concentric shear planes within the vortex and larger particles of the powdered medication tend to have sufficient momentum to escape these vortices and collide with other particles, thereby causing de-agglomeration of the larger particles, provided they do not impact on the walls of the container 16. Further pressure gradients between the inlet and outlet vents formed by air/medication ports 36M have also been observed to accelerate some particles in concentric paths around the needle.

It was noted that the penetration of the container 16 by the needle 36 resulted in small openings between the container 16 wall and the wall of the needle 36 at the entry end of the container 16, that is, at the end of the container 16 initially penetrated by the needle 36, and at which some accumulation of medication particles was observed. It was unclear, however, to what extent these small openings contributed to the airflow within the capsule. For example, some particles appeared to travel towards the back end of the capsule, turn, and accelerate out in an elliptical path, but whether this was caused by venting from the small openings at the back of the container 16 or from induced vortices could not be determined. As a result, a needle 36 variant having small openings at the back end of the container 16, that is, at the end of the container 16 initially penetrated by the needle 36, was developed to study the effects of possible venting at the back of the container, and will be discussed in a following description of that needle 36 variant.

Lastly with regard to the basic form of needle 36, it has been found that it is necessary that the air/medication ports 36M be located sufficiently forward toward the tip of the needle 36 to insure that an adequate proportion of one or both air/medication ports 36M extend past the end of the container 16 and into the lower air passage 20. If, for example, the air/medication ports 36M are located to overlap the end of the container 16 to an excessive degree, there is a risk that a "chad" or flap 16D of container 16 wall pushed outward by the penetration of the needle 36 will obscure and block one or both of the air/medication ports 36M to an unacceptable extent. The blockage of one or both air/mediation ports 36M will unacceptably limit the flow of air from lower air passage 20 into the needle 36 and prevent an adequate dispensing of the medication.

In addition, the tip of the needle 36 must not extend so far past the end of the container 16 that the tip of needle 36 contacts the end of container chamber 14B as this result may, for example, prevent the proper actuation of body 14 and mouthpiece 12 or distort the relationship between the needle 36 and the container 16 by, for example, bending, tilting or otherwise distorting the needle 36.

Next, it will be noted that in the embodiment of a needle 36 as illustrated in FIG. 11, for example, the penetration of the end wall of the container 16 by pyramidal puncture point 36P results in the creation of four "flaps" 16D of container wall material. The flaps 16D are attached generally to the edge of the penetration hole and are rotationally oriented with respect to the point 36P so that the flaps are aligned with the faces of the point 36P pyramid and are separated by along lines that are aligned with the vertices, or lines of joining, between adjoining faces of the pyramid. In the embodiment of a needle 36 as illustrated in FIG. 11A, the four faced pyramidal puncture point 36P is rotationally oriented on hollow tubular body 36T so that two opposing faces of the point 36P are aligned with the two opposing air/medication ports 36M. This rotational orientation of point 36P thereby results two of the flaps created when the point 36P pierces the end wall of the container 16 being generally aligned with the air/medication ports 36M, and the possibility that these flaps will at least partially block or otherwise restrict the flow of air into the air/medication ports 36M.

Figure 12:
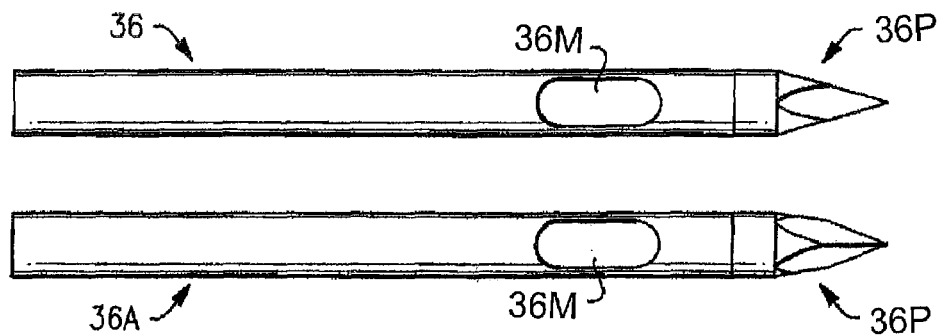
FIG. 12 is a diagrammatic illustration of a basic configuration pyramidal point needle having tip vertices aligned with the air/medication ports.

For this reason, and as illustrated in FIG. 12, a first variant needle 36A was developed wherein the pyramidal tip 36P was rotated 45° with respect to the orientation of the needle 36 of FIG. 11A so that the vertices between the flat faces of pyramidal first variant needle 36A tip 36P were aligned with the air/medication ports 36M, thereby reducing the potential or actual interference of the flaps 16D of container 16 wall material with the flow of air into the air/mediation ports 36M. It was found that this design resulted in somewhat stronger vortexes than those formed in the needle 36 design of FIG. 11A, and that the somewhat improved movement and rotation provided by the stronger vortexes provided higher de-agglomeration of the particles. It was also found, however, that the higher momentum imparted to the powder by the stronger vortexes caused somewhat more particles to impact on the capsule walls. The results in terms of medication delivery and air flow were found to be similar to that in the needle 36 design of FIG. 11A, but provided somewhat greater consistency and less deviation in the delivery of medication, coupled with a reduced percentage of delivery due to powder impaction.

Figure 13:
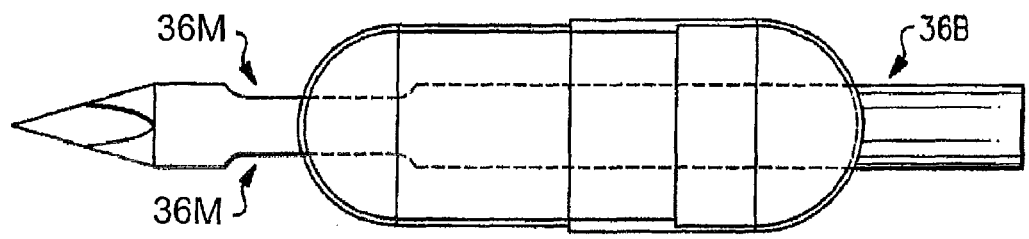
FIG. 13 is a diagrammatic illustration of a needle having longitudinally extended and shifted air/medication ports.

Referring to FIG. 13, therein is illustrated a second variant needle 36B wherein the air/medication ports 36M have been longitudinally extended and shifted toward the tip of needle 36B to increase the flow of air into the needle 36B from lower air passage 20. As described previously with reference to FIGS. 7A-7D, in an exemplary embodiment the needle 36B may be approximately 1 inch long and 0.11 inch in diameter with an inner bore diameter of approximately 0.08 to 0.09 inch and each air/medication port 26G is may be approximately 0.15 inch long. In the present variation of needle 36B, again for example, air/medication ports 36M may be lengthened by approximately 0.050 inch and moved toward the tip of needle 36B by approximately 0.010 inch. It was found that this second variant of a needle 36B had significantly improved medication delivery rates and delivery percentages, which appears to be a consequence of the increased capability to draw large amounts of air through the needle at high Velocity because of the larger exposed areas of the air/medication ports 36M outside of container 16, that is, to the exterior air through lower air passage 20. Stated another way, if the total pressure of the system is conserved according to the Bernoulli Equation, then increasing the dynamic pressure along a streamline by accelerating the flow will lower the static pressure of the fluid, which will cause an very low pressure in the container 16 and an increased draw of powder from the container 16. This is essentially an illustration of the Venturi Effect and, because of the velocities and speeds involved, it allows the container 16 to be cleared very rapidly and completely.

Figure 14:
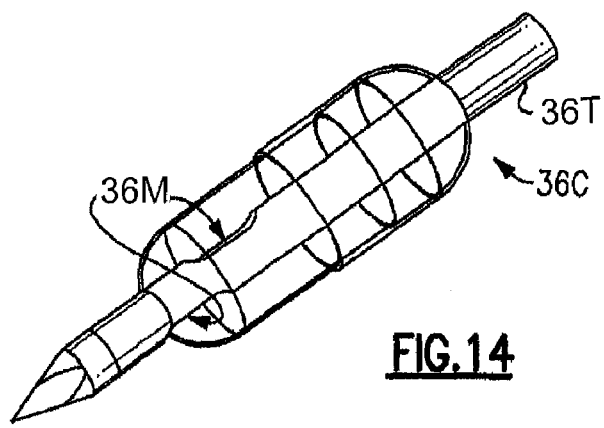
FIG. 14 is a diagrammatic illustration of a needle having asymmetrically located air/medication ports.

Referring to FIG. 14, therein is illustrated a third variant needle 36C wherein air/medication ports 36M are asymmetrically located along the length of needle body 36T, with one port 36M being located closer to point 36P than the other to improve airflow consistency. In this configuration the port 36M closest to point 36P is forced to function as an airflow input port allowing airflow into the container 16 from lower air passage 20. At the same time, the rearmost port 36M, that is, the port 36M further from point 36P, is contained entirely within the container 16 and is thereby forced to function as an outlet for the flow of air and medication from the container 16 and into the interior passage of the needle 36C. This configuration was observed to result in the formation of a strong vortex over the rearward port 36M, that is, the "container drain" port 36M, and the formation of other strong induced vortices in the rear portions of the container 16, that is, the regions of the container 16 around the initial penetration opening. It was observed that vortices resulted in very high de-agglomeration of the medication particles through vortex shearing and particle collisions. It was also observed that in some instances the powder particles achieved sufficient momentum to escape the vortices and impact on and adhere to the walls of the container 16 and that in some instances there was an apparent "dead spot" located at the rear end of the container 16 due to a lack of air circulation in that area. In most trails, however, the container 16 was completely cleared of the particles of medication powder.

Figure 15:
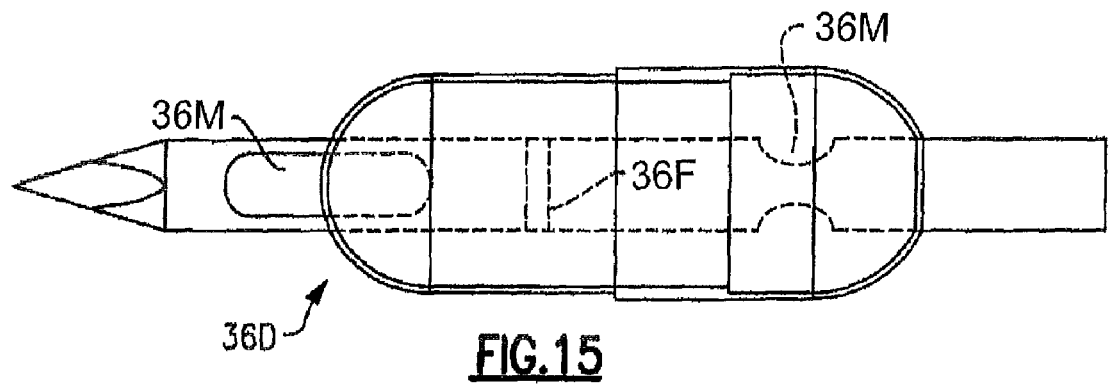
FIG. 15 is a diagrammatic illustration of a needle having forward and rearward pairs of air/medication ports separated by an internal baffle.

Referring to FIG. 15, therein is illustrated a fourth variant needle 36D that is "rear vented" by a second pair of air/medication ports 36M located toward the rear end of the needle 36D, that is, toward the end opposite point 36P of needle 36D. The rear pair of ports 36M is in addition to the first pair of air/mediation ports 36M located toward forward end of the needle 36D, that is, toward the end of needle 36D toward point 36P, and is located within the length of the container 16. Additionally an internal baffle 36F may be located between the first and second pairs of air/medication ports 36M and within the interior length of container 16. The forward pair of air/medication ports 36M thereby function as an airflow input port allowing airflow into the container 16 from lower air passage 20 and the rearward pair of air/medication ports 36M function as an outlet for the flow of air and medication from the container 16 and into the interior passage of the needle 36C. The resulting airflow path requires air to enter the container 16 at the forward pair of air/medication ports 36M and to traverse the entire length of the interior of the container 16 before exiting into needle 36D at the rear pair of air/medication ports 36M, thereby effectively eliminating airflow "dead spots" within the container 16. Tests shows that the medication particles in the container 16 were cleared within a very short period, on the order of 350 ms, and that approximately 75% of the medication was consistently delivered to the patient. It was also observed that in some instances the medication particles were drawn or swept toward the rear pair of air/medication ports 36M with sufficient velocity to impact on and adhere to the back end of the container 16.

Figure 16:
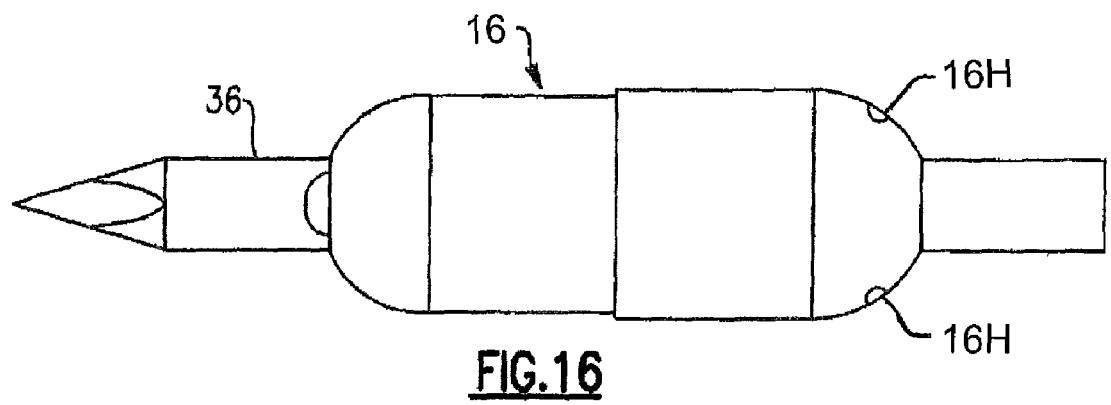
FIG. 16 is a diagrammatic illustration of a medication container having rear vent ports.

An alternate implementation of a container 16 wherein the container 16 itself is rear vented to the exterior air is illustrated in FIG. 16. A shown therein, the container 16 is vented by a plurality of vent holes 16H through the wall of the container 16 around the rear end of the container 16, that is, around the end of container 16 opposite point 36P of the needle 36, and in locations where vent holes 16H will connect with exterior air through bypass vent passages 20V. This configuration of a container 16 was found by experiment to deliver over 76% of the medication particles to a patient within approximately 400 milliseconds without any "dead spots" within the container 16.

Figure 17:
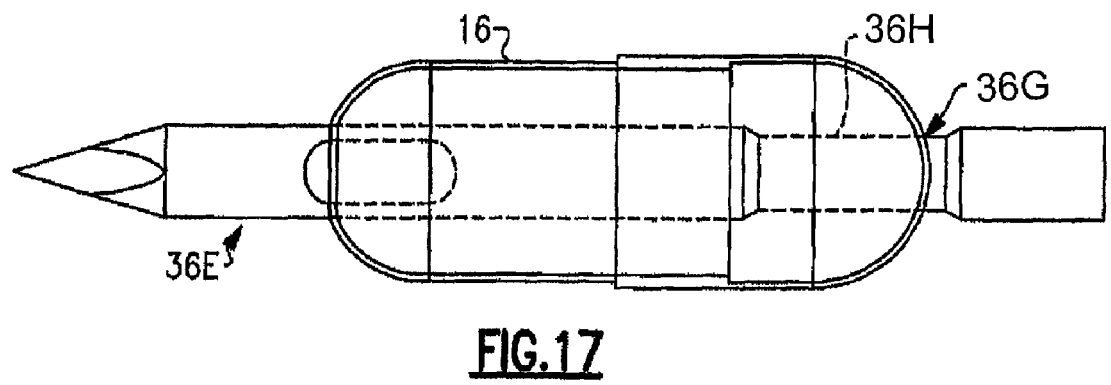
FIG. 17 is a diagrammatic illustration of a basic configuration needle having a reduced rearward circumference to form a rear vent port upon penetration of the medication container by the needle.

A further alternative embodiment of a rear vented needle 36/container 16 structure is illustrated in FIG. 17. In this variant, the exterior diameter of needle 36E is reduced in a region 36H that extends longitudinally between the interior and exterior sides of the rear end wall of the container 16 when the inhaler 10 is in the actuated state. As has been illustrated herein above, the penetration of the rear end wall of the container 16 by the needle 36E will result in an opening through the end wall having a diameter approximately the same as that of the needle 36E. The reduction in the exterior diameter of the needle 36E in region 36H will thereby provide a rear vent passage 36G between the interior circumference of the penetration opening through the end wall and the reduced outer diameter of needle 36E in the region 36H.

It has been shown that the needle 36E configuration illustrated in FIG. 17 will result in a large pressure difference and a high air flow between rear vent passages 36G and the air/medication ports 36M located toward the tip end of the needle 36E. The resulting pressure gradient carried essentially all of the medication powder particles from the rear end of the container 16 to the air/medication port 36M end of the container 16 at high velocities, forming free vortices over the air/medication ports 36M and drawing the medication particles into the needle 36E and to mouthpiece 12. In some instances, the velocity of the airstream and the powder carried therein was sufficiently high to result in either permanent or temporary impaction of the powder on the opposite container 16 wall. It was also found that rear vent passages 36G resulted in less total air circulation throughout the container 16 and caused fewer particle collisions, and thus less de-agglomeration of the particles, because the vortices had less time to stabilize before the container 16 had been cleared of medication.

H. Container 16 Alignment and Retention Issues

It was consistently observed during the above discussed tests and experiments with various configurations and implementations of needles 36 and containers 16 that off-center punctures and non-centered or eccentric positioning of the needle 36 in the penetrated containers 16 consistently resulted in inconsistent and reduced efficiency in the delivery of medication to mouthpiece chamber 12A. It was also observed that off-center punctures and non-centered or eccentric punctures of the container 16 was generally due to the container 16 shifting or otherwise moving or distorting during puncture of the container 16 by the needle 36, but may also be caused by shifting or distortion of the needle 36. These effects are illustrated in FIG. 18A-18D, wherein FIGS. 18A and 18B illustrated end and side view of a centered puncture of a container 16 by a needle 36, and FIGS. 18C and 18D illustrate end and side views of a non-centered puncture.

Rigid control of the container 16 and of the needle 36 by rigidly holding the container 16 and the needle 36 in concentric orientation during activation of the inhaler 10 is therefore necessary in order to obtain correct, centered punctures by the needle 36 and the maximum and optimum delivery of medication.

I. Conclusions

In conclusion, the basic needle 36 configuration as illustrated in FIG. 11A performed well and consistently as regards the clearing of medication from the container 16 and the delivery of the medication to the user, and in de-agglomerating all of the medication powder examples tested. As described above, this configuration of needle 36, referred to as a pyramidal needle 36, is comprised of a hollow tubular body 36T terminated by a pyramidal puncture point 36P and having two air/medication ports 36M located on opposite sides of the body 36T in the region toward the point 36P. As has been discussed, the air/medication ports 36M are located along body 36T of the needle 36 so that after the needle 36 has fully penetrated the container 16 approximately 9/10ths of the areas of air/medication ports 36M are within the container 16 and approximately 1/10th of the areas of air/medication ports 36M communicate with lower air passage 20.

The various modifications, variants and alternate embodiments of needle 36, including the above discussed related modifications to the container 16, all resulted in one or more trade-offs of potential benefits and drawbacks. For example, extending and shifting the locations of air/medication ports 36M as illustrated in FIG. 13 resulted in higher delivered dosages of the medication and venting of the container 16, either by means of vents in the container 16 or of rear vents made by the configuration of the needle 36 outer contour, resulted in relatively complete and rapid clearing of the powder and relatively high delivered dosages. The increased airflow velocity, however, caused more impaction of the powder against the container wall, does not allow the vortices time to stabilize the increased speed causes more impaction, does not allow the vortices enough time to stabilize, and reduces the amount of time available to de-agglomerate the powder, all of which results in faster delivery of the medication but lower medication delivery percentages and greater inconsistency in the amount delivered.

The vertex-aligned needle tip configuration as illustrated in FIG. 12 in turn provides better and more consistent airflow throughout the container 16, but the faster airflow causes slightly more impaction and adherence of medication particles to the walls of the container and thereby reduced medication delivery.

The asymmetric needle configuration illustrated in FIG. 14 yielded much more consistent vortex formation. The vortex themselves were more intense and provided greater de-agglomeration, but the single inlet was observed to allow small dead spots in the rear of the capsule and the higher particle velocities caused some impaction and adhesion of medication particles with the walls of the container. The dead spots and volumes of impacted particles, however, were not significantly greater than those seen by the base configuration of the needle 36 as illustrated in FIG. 11.

The results obtained with the needle 36 and container 16 configurations shown in FIGS. 15, 16 and 17, that is, needles 36 having forward and rearward sets of air/medication ports 36M and an internal baffle 36F, or a circumferential rear vent 36G formed between the needle 36 and container walls, or the rearwardly vented container 16H, all provided similar observed results. In particular, in each instance the rate of flow of medication particles from the container was notably increased, by approximately two times compared to the basic needle 36 configuration of FIG. 11A. The higher flow rate and reduced medication extraction time, however, reduced vortex formation, thus reducing de-agglomeration of the mediation particles, and resulted in higher rates of particle impaction with the wall of the container, resulting in a higher percentage of trapped medication particles.

Lastly, the above described experiments included observation of the medication powder and air flow rates and patterns in mouthpiece chamber 12A and it was consistently observed that the powder flow initialized as a focused jet emanating from the needle. It was further observed that within a few milliseconds the jet began to diffuse and turn back to circulate within mouthpiece chamber 12A, most probably due to a lower pressure adjacent the mouthpiece chamber 12A walls. It was also seen that there was little additional de-agglomeration of the medication particles within the needle itself 36, thereby indicating that the flow of air and powder within the needle is most probably laminar and non rotational.

J. Implementations Delivering Multiple Concurrent Doses of Medication

Continuing with further alternate embodiments and implementations of a medication inhaler 10 of the present invention, it is often desirable to be able to administer multiple doses of medications simultaneously or concurrently, that is, at the same time and in the same manner as a single dose as described above. For example, a medication inhaler 10 capable of administering multiple doses of medication concurrently may administer two or more separate medications at the same time, or may administer multiple doses of the same medication at the same time. In the latter case, the size of the delivered dose may be controlled by selecting one or more medication capsules from among a set of medication capsules having standardized doses rather than requiring that a medication capsule be fabricated for each possible size of dosage.

Referring to FIG. 19A, an exemplary multiple concurrent dose medication inhaler 10, allowing the delivery of a medication or medications from up to two medication containers or capsules 16, is illustrated therein as a first medication container 16A and a second medication container 16B.

As shown, a multiple concurrent dose medication inhaler 10 includes a mouthpiece 12 and a main body 14, as described herein above with regard to other embodiments of the multiple concurrent dose medication inhaler 10 of the present invention. As previously described, the body 14 generally forms a structure for enclosing the first and the second medication containers 16A and 16B and, as shown in FIG. 19A typically has a cylindrical main body 14A that includes an axially extending second container chamber 14B having a length and a diameter which is sized and shaped to receive, accommodate and enclose the second medication container 16B. The body 14 includes one or more air passages 18 for drawing air into and through the first and the second medication containers 16A and 16B, which are represented in FIGS. 19A and 19B as including a lower vertical air passage 18A extending from the bottom end of the container chamber 14B and intersecting a horizontally extending air passage 18B that connects with an air source located outside the body 14 to provide a lower air passage 20 extending between the exterior air and into the bottom end of the container chamber 14B. It should be noted, however, that as described previously above the alternate configurations of lower air passages 18A, 18B and/or 20 may be used. For example, there may be only one air passage 18B intersecting lower vertical air passage 18A or possibly there may be two or more air passages 18B connecting the outside air with the lower vertical air passage 18A. In yet other embodiments, one of more air passages 18B may intersect lower vertical air passage 18A at an acute or slanted angle, rather than at a right angle as generally shown, or the lower vertical air passage 18A may extend along a straight path and communicate with the outside air, or lower vertical air passage 18A or one or more air passages 18B may connect with the outside air through a "torturous", curved or zig-zagged path, rather than as a straight path. In yet other embodiments, the air passage connection between lower vertical air passage 18A and the outside air may take the form of one or more slots aligned parallel to, perpendicular to or at an angle or angles with lower vertical air passage 18A, etc.

As shown in FIGS. 19A-19C, the body 14 includes a cylindrical wall 14C that surrounds the container chamber 14B and that extends vertically upward above the upper end of the container chamber 14B, wherein, in the illustrated embodiment, the upward extension has an exterior diameter that is less than the exterior diameter of the main part of the body 14A. As shown, the interior of the cylindrical wall 14C forms an upward end of the container chamber 14B and, as discussed below, the cylindrical wall 14C sealingly mates with a corresponding portion of the mouthpiece 12. It should be recognized, however, as will be apparent from FIG. 19A and the previous descriptions of the multiple concurrent dose medication inhalers 10, that the exterior diameter of the cylindrical wall 14C may, for example, be equal to that of the main body 14A, with corresponding adaptations to the mating contours of the mouthpiece 12.

Referring now to the mouthpiece 12, the mouthpiece 12 generally provides a mechanism for opening the first and the second medication containers 16A and 16B residing within the body 14 and for delivering the medication contained therein to a user. As illustrated in FIG. 19A, the mouthpiece 12 includes two axially connected interior spaces, including a mouthpiece chamber 12A in the upper portion of the mouthpiece 12 and a body chamber 12B in the lower portion of the mouthpiece 12, with the two chambers being axially connected through a needle passage 12C. As shown, the interior of the body chamber 12B and the lower part of the needle passage 12C are shaped and sized to receive the upper portion of the main body 14A and the cylindrical wall 14C, thereby forming an enclosed protective container chamber 14B in which the first and the second medication containers 16A and 16B can reside.

As also illustrated in FIG. 19A and as previously described above, the mouthpiece 12 includes a hollow medication delivery needle 26 that functions to open each of the axially aligned first and second medication containers 16A and 16B, thereby making the medication accessible to the patient or user, and as a delivery mechanism for extracting the medication contained within each of the first and the second medication containers 16A and 16B and delivering the medication to the user or patient. As shown, an upper section of the medication delivery needle 26 resides in needle passage 12C, with the upper end 26U of the medication delivery needle being located in the region of the intersection of the needle passage 12C and the mouthpiece chamber 12A. The upper end of the delivery needle 26 may be located over an axial range extending from within the needle passage 12C to within mouthpiece chamber 12A. As shown, and as discussed previously, the lower end 26L of the medication delivery needle 26 extends downward and is located for piercing the medication containers 16A and 16B and forming a passage for the delivery of the medication when the mouthpiece 12 and the main body 14 are axially moved relative to one another, e.g., "telescoped," into the activated second position.

Now considering the container chamber 14B in further detail, as illustrated in FIG. 19A, the container chamber 14B includes an first container chamber 14D for receiving a first medication container 16A and a second container chamber 14E for receiving a second medication container 16B, with the first and the second container chambers 14D and 14E having diameters and lengths, respectively, adapted to the diameters and the lengths of the first and the second medication containers 16A and 16B to be accommodated therein.

In the exemplary embodiment of the multiple concurrent dose medication inhaler 10, illustrated in FIG. 19A, the first and the second medication containers 16A and 16B are of different diameters and have a different length. The inner diameter of the first container chamber 14D is sized to closely receive and accommodate the outer diameter of the first medication container 16A and the inner diameter of the second container chamber 16B is sized to closely receive and accommodate the outer diameter of the second medication container 16B, so that the first and the second medication containers 16A and 16B are supported in appropriate alignment with so as to be pierced by the needle 26 when the inhaler 10 is actuated into its second position.

As also shown, the inner diameter of the first container chamber 14D at the end of the first container chamber 14D toward second container chamber 14E, that is, in the direction of motion of the needle 26 in piercing the first medication container 16A, is reduced in diameter to form a first chamber shoulder 14F. The radially inward extension of the first chamber shoulder 14F is sufficient, and is formed, to axially support the first medication container 16A when being pierced by needle 26. The inner diameter of the first chamber shoulder 14F, however, is sufficiently large to allow the passage of second medication container 16B and is thus of at least approximately the same diameter as the second container chamber 16B.

In a similar manner, the inner diameter of the second container chamber 14E at the end of the second container chamber 14E located away from the first container chamber 14D, that is, in the direction of motion of the needle 26 during piercing of the first medication container 16B, is reduced in diameter to form a second chamber shoulder 14G. The radially inward extension of the second chamber shoulder 14G is sufficient, and is formed, to axially support first medication container 16A when being pierced by the needle 26.

With reference now to the embodiment of the multiple concurrent dose medication inhaler 10 illustrated in FIG. 19B, the first and the second medication containers 16A and 16B illustrated therein are of the same diameters, but have different length. According to this embodiment, the inner diameters of the first and the second container chambers 14D and 14E are again accordingly sized to closely fit the outer diameters of the first and the second medication containers 16A and 16B, thereby supporting the first and the second medication containers 16A and 16B in appropriate alignment with the needle 26. Because the first and the second medication containers 16A and 16B are generally of the same diameter, however, the first and the second container chambers 14D and 14E are of the same diameter so that the container chamber 14B is generally of a uniform diameter throughout its length.

As shown in this embodiment, the inner diameter of the second container chamber 14E at the end of the second container chamber 14E located away from the first container chamber 14D, that is, in the direction of motion of the needle 26 during piercing of the first medication container 16B, is again reduced in diameter to form the second chamber shoulder 16BD which axially supports the first medication container 16A when being pierced by the needle 26. As may be seen, however, and because the medication containers 16A and 16B are generally of the same diameter, the inner diameter of the first container chamber 14D, at the end of the first container chamber 16BA located toward the second container chamber 14E, that is, in the direction of motion of the needle 26 during piercing of the first medication container 16A, cannot be reduced in diameter to form a first chamber shoulder 16F to axially support first medication container 16A.

There are, however, a number of possible methods by which axially support may be provided for the first medication container 16A while still allowing the medication container 16B to freely pass along the length of container chambers 14D and 14E to its final position. For example, the medication container 16B may provide sufficient axial support for the first medication container 16A by allowing the first medication container 16A to be supported by end-to-end contact with the second medication container 16B.

In the embodiment illustrated in FIG. 19B, the second medication container 16B again provides axial support for the first medication container 16A, but a container spacer 14S is inserted into the container chambers 14D and 14E, between medication containers 16A and 16B, to provide a greater bearing surface between the first and the second medication containers 16A and 16B.

As illustrated, and for example, the container spacer 14S is generally cylindrical in shape with a diameter which is slightly smaller than the inner diameter of the container chamber 14D so as to allow container spacer 14S to be easily located and positioned within the container chamber 14. A first one of the opposed axial end faces of the container spacer 14S is generally concave and shaped so as to conform to the shape of the end face of the first medication container 16A, while the other opposed axial end face of the container spacer 14S is generally concave and shaped so as to conform to the shape of the end face of the second medication container 16B, thereby distributing the pressure between the facing ends of the first and the second mediation containers 16A and 16B over a relatively large portion of the end surfaces of the first and the second medication containers 16A and 16B. The container spacer 14S will also include an axial needle passage 14N extending generally centrally through the body of the container spacer 14S to facilitate passage of the needle 26 therethrough. In general, the second medication container 16B will typically be inserted into container chamber 14, followed by container spacer 14S and finally by the first medication container 16A. As indicated by the dashed lines associated with axial needle passage 14N in FIG. 19B, needle passage 14N may have a generally tapered or funnel-like cross section or a tapered or funnel entry to facilitate the entry of a needle 26, 36 into and through needle passage 14N.

In a still further embodiment of the multiple concurrent dose medication inhaler 10 as illustrated in FIG. 19C, the container chambers 14D and 14E, that is, the container chamber 14B, is designed as described just above to accommodate medication containers 16A and 16B of the same diameter, although possibly of different axial lengths, but is adapted to accommodate medication containers 16A and 16B of smaller diameters by the insertion of a container adapter 14H.

FIG. 19C illustrates the structure and use of the container adapter 14H which is inserted into second container chamber 14E of container chamber 14B, although it will be recognized that the container adapter 14H could instead be inserted into first container chamber 14D, so that the smaller diameter medication container 16B could be located in first container chamber 14D rather than in second container chamber 14E, while the larger diameter medication container 16A is located in second container chamber 14E.

As shown, the container adapter 14H is generally cylindrical in shape, having an outer diameter which is to be closely received by and within the inner diameter of the container chambers 14D and 14E, and includes a generally cylindrical container chamber 14I having an internal diameter which closely receives the outer diameter of a second medication container 16B.

As indicated by the dashed lines associated with axial needle passage 14N in FIG. 19B, container adapter 14H includes upper and lower needle passages 14N for the passage of a needle 26, 36 therethrough. The second medication container 16B is thereby supported within the container chamber 14I and the container adapter 14H supported in the container chamber 14D or 14E so that the second medication container 16B is supported in suitable and appropriate alignment with the needle 26, 36.

As indicated by the dashed lines associated with upper and lower needle passages 14N in FIG. 19C, one or both of the upper and lower needle passages 14N may have a generally tapered or funnel-like cross section or a tapered or funnel entry to facilitate the entry of a needle 26 or 36 into and through needle passage 14N. It will also be noted that, as again indicated in FIG. 19C by dashed separation lines 14O, the container adapter 14H will typically be separable into two sections to allow a medication capsule 16 to be inserted into the container adapter 14H, with the two sections then being reassembled to allow the container adapter 14H with the enclosed medication capsule 16 to be inserted into the first or second container chamber 14D or 14E. As illustrated, the container adapter 14H may be separated into two longitudinal sections by a separation line 14O joint extending axially along the length of container adapter 14H or by transverse separation line 14O joint extending transversely to the axis of the container adapter 14. In other instances, for example, the upper end of the container adapter 14H may be open for the full inner diameter of the container adapter 14H, with the upper end of then being closed and the upper end of the medication capsule 16 being supported by a container spacer 14S.

As also illustrated, the container adapter 14H is oriented within container chamber 14B so that a first end 14J of the container adapter 14H is positioned adjacent the medication container 16A. The exterior side of the first end 14J of container adapter 14H is generally concave and generally shaped to mate with the shape of the mating end of the medication container 16A with an axial opening therethrough to allow the passage of a smaller diameter medication container 16B and the needle 26. The shoulder 14K formed by the first end 14J of the container adapter 14H thereby provides axial support between the container adapter 14H and the first medication container 16A. As also indicated, the inner side of the first end 14J of the container adapter 14H is typically generally shaped to the form of the corresponding end of the second medication container 16B to provide support for the second medication container 16B. The second end 14L of the container adapter 14H has an opening therethrough to accommodate the needle 26 and the exterior side of the second end 14L of the container adapter 14H is generally shaped to the corresponding inner side of the end of container chamber 14B. The inner side of second end 14L is again typically generally shaped to the form of the corresponding end of the second medication container 16B so as to provide support for the second medication container 16B.

According to this embodiment of the present invention, the second medication container 16B may be inserted into a container adapter 14H either before or after the container adapter 14H has been inserted into the container chamber 14B of the inhaler 10. In a similar manner, the medication container 16A and the container adapter 14H are inserted into the container chamber 14B in any order, with the second medication container 16B being inserted into the container adapter 14H either before the container adapter 14H is inserted into the container chamber 14B or after the container adapter 14H has been inserted into the container chamber 14B.

Next considering needle 26, 36 in the above described embodiments of the multiple concurrent dose medication inhaler 10, it will be appreciated that the needle 26, 36 of the multiple concurrent dose medication inhaler 10 may generally take any of the forms described above, given the adaptation described below to accommodate two or more medication containers 16 axially positioned in the container chamber 14 of the inhaler 10. For purposes of following discussion and description, however, the exemplary embodiments of the multiple concurrent dose medication inhaler 10, as illustrated in, for example, FIG. 19A, are shown as incorporating a needle 36 generally similar to that described herein above with reference to FIGS. 8A-8D. Adaptations of the described embodiment to employ, for example, needles 26 having, for example, a tip structure similar to that described above with reference to FIGS. 2A-2E will, however, be well understood by those of ordinary skill in the art in view of the disclosure of this specification.

As shown in FIG. 19A and, the needle 36 employed in this embodiment of the multiple concurrent dose medication inhaler 10 is a pyramidal delivery needle 36, as previous described with reference to FIGS. 8A-9D. As described, a pyramidal point delivery needle 36 comprises a hollow tubular body 36T having a lower end terminated and closed by a pyramidal puncture point 36P and at least two spaced apart air/medication ports 36M, wherein each of the air/medication ports 36M is located along the body 36T of the needle 36 so that when the illustrated inhaler 10 is in the actuated state, that is, the mouthpiece 12 and the body 14 are pushed together so that the needle 36 penetrates both the first and the second medication containers 16A and 16B to the maximum extent, each respective air/medication port 36M is located partly within the first or the second medication contained 6A or 16B and partly within and connecting to the lower air passage 20. For example, when the inhaler 10 is fully actuated, approximately 9/10ths of each respective port 36M is located within the respective first or second medication container 16A or 16B and approximately 1/10th communicates with lower air passage 20. The air/medication ports 36M located in the lower portion of the needle 36, that is, generally adjacent to the pyramidal puncture point 36P so that the ports 36M are located to be within both the container 16B and lower air passage 20 operate as described above with regard to FIGS. 8A-8D and extract the medication from the medication container 16A or 16B located in second container chamber 14E.

As shown in FIG. 19A and from the preceding descriptions of the needle 36, the needle 26, 36 is adapted for use in the multiple concurrent dose medication inhaler 10 by the inclusion of air/medication port or ports 36M. Air/medication port or ports 36M are located along the length of the needle 36 so that when the inhaler 10 is in the actuated state or second position, the air/medication port or ports 36M are located partly within the medication container 16A or 16B residing in the first or second container chamber 14D, 14E, and partly within and connecting to the air passage through container chambers 14D and 14E, with approximately 9/10ths of the port or ports within the medication container 16A or 16B and approximately 1/10th communicating with the air passage. Air/medication port or ports 36M thereby operate with respect to the medication container 16A or 16B residing in the first or second container chamber 14D 14E to extract the medications from the medication container 16A or 16B in a manner similar to that of the air/medication port or ports 36M located with the medication container 16A or 16B located in container chamber 16B.

Lastly, the above described embodiments of multiple concurrent dose medication inhalers 10 may be extended to accommodate a third or a fourth, or possibly more, medication containers which are generally aligned end-to-end with one another. The steps, methods and structural adaptations required to extend the structure of a multiple concurrent dose medication inhaler 10 as described herein above will, however, readily apparent and well understood by those of ordinary skill in the relevant arts after perusal of the descriptions and drawings discussed herein above. Accordingly, only the following very brief discussion of the same is provided.

Figure 20A:
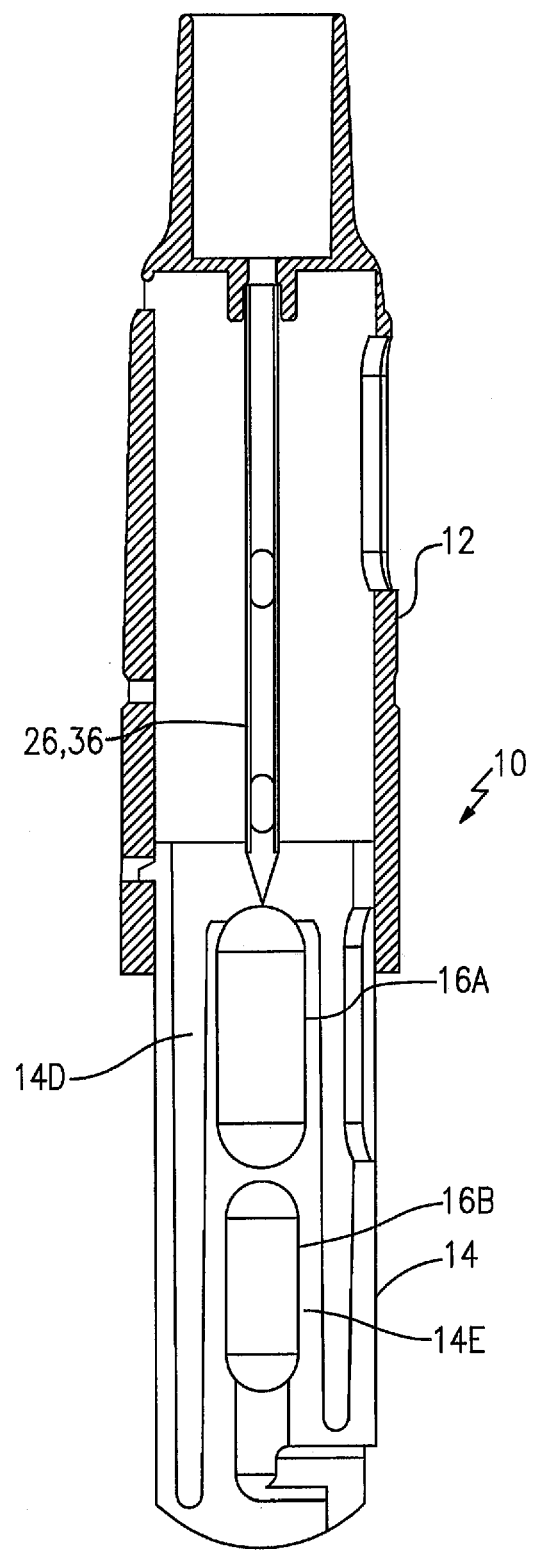
Figure 20B:
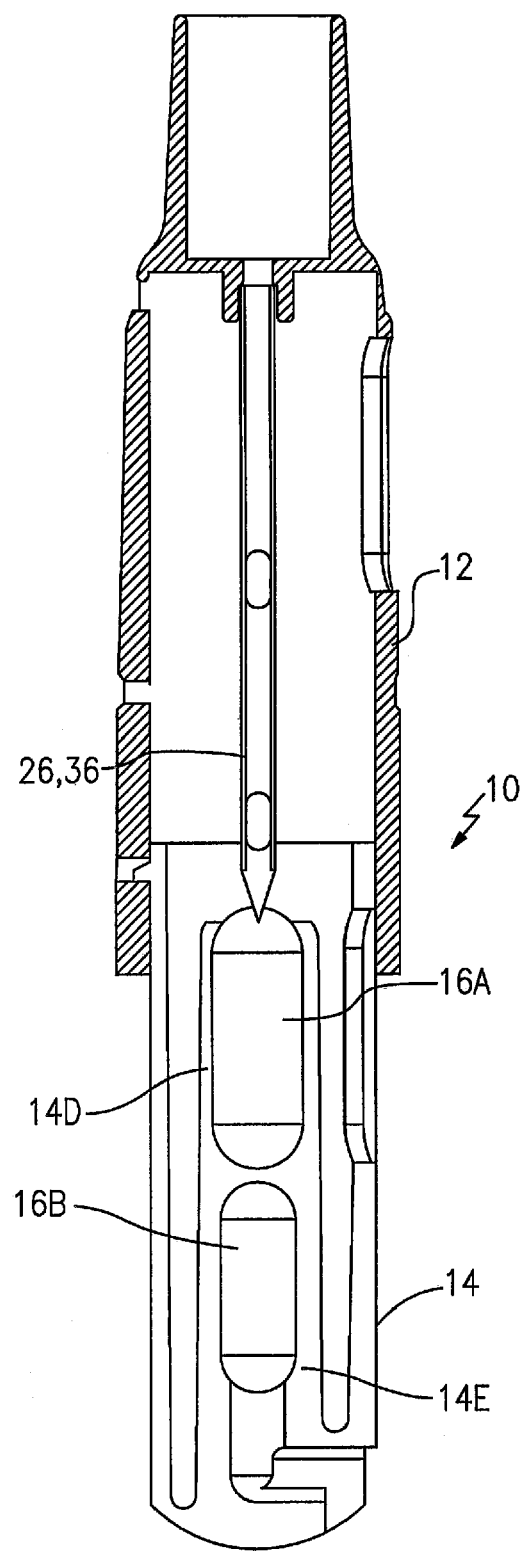

Referring to FIGS. 20A, 20B, 20C and 20D, therein is illustrated successive steps in the operation of a multiple concurrent dose medication inhalers 10. FIG. 20A illustrates the inhaler 10 in the initial position, FIG. 20B illustrates the stage wherein the needle 26/36 begins to penetrate the upper medication capsule 16, FIG. 20C illustrates the stage when the needle 26/36 has entered but not fully penetrated the upper medication capsule 16, and FIG. 20D illustrates the final stage when the needle 26/36 has penetrated both medication capsules 16 and the medications are delivered to the patient.

With reference to FIG. 21A, a multiple concurrent dose medication inhaler, having first, second and third medication chambers 14D, 14E and 14P arranged within the main body 14 end-to-end sequentially one after the other, is diagrammatic shown in this Figure. Each of the first, the second and the third medication chambers 14D, 14E and 14P respectively accommodates the first, the second and the third medication containers 16A, 16B and 16E. According to this embodiment, the needle 36 has three spaced apart air/medication ports 36M wherein each of the air/medication ports 36M is located along the body 36T of the needle 36 so that when the illustrated inhaler 10 is in the actuated state, that is, the second position in which the mouthpiece 12 and the body 14 are pushed together so that the needle 36 penetrates the first, the second and the third medication containers 16A, 16B and 16E to the maximum extent, each respective air/medication port 36M is respectively located partly within (approximately ⁹/₁₀th within) the first, the second or the third medication containers 16A, 16B or 16E and partly within and connecting to the lower air passage 20 to facilitate concurrent delivery of the medication from all three of the medication containers 16A, 16B or 16E.

With reference to FIG. 21B, a multiple concurrent dose medication inhaler, having first, second, third and fourth medication chambers 14D, 14E, 14P and 14Q arranged within the main body 14 end-to-end sequentially one after the other, is diagrammatic shown in this Figure. Each of the first, the second, the third and the fourth medication chambers 14D, 14E, 14P and 14Q respectively accommodates the first, the second, the third and the fourth medication containers 16A, 16B, 16E and 16F. According to this embodiment, the needle 36 has four spaced apart air/medication ports 36M wherein each of the air/medication ports 36M is located along the body 36T of the needle 36 so that when the illustrated inhaler 10 is in the actuated state, that is, the second position in which the mouthpiece 12 and the body 14 are pushed together so that the needle 36 penetrates the first, the second, the third and the fourth medication containers 16A, 16B, 16E and 16F to the maximum extent, each respective air/medication port 36M is respectively located partly within (approximately ⁹/₁₀th within) the first, the second, the third, or the fourth medication containers 16A, 16B, 16E, or 16F and partly within and connecting to the lower air passage 20 to facilitate concurrent delivery of the medication from all four of the medication containers 16A, 16B, 16E or 16F.

Figure 21C:
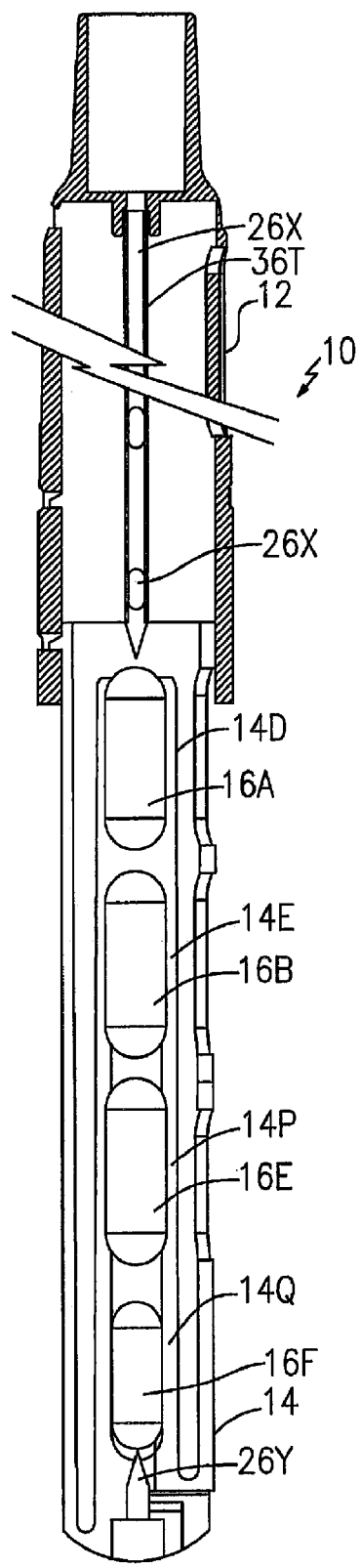
FIG. 21C is a diagrammatic sectional view of the multiple concurrent dose medication inhaler having four medication chambers arranged end-to-end sequentially one after the other which are to be dispensed via a pair of opposed dispensing needles.

Referring now to FIG. 21C, a further embodiment of the inhaler 10, quite very similar to the embodiment discussed above with reference to FIG. 21B will now be described. As this embodiment is very similar to the previously discussed embodiment, only the differences between this embodiment and the embodiment of FIG. 21B will discussed in detail. The primary variation of this embodiment is that medication delivery needle 26 is a double, instead of a single, medication delivery needle 26Z which comprises an upper delivery needle 26X and a lower delivery needle 26Y. During dispensing, the upper delivery needle 26X is designed so as to penetrate completely through the first, the second and the third medication containers 16A, 16B and 16E and only partially through the fourth medication container 16F while the lower delivery needle 26Y is designed to partially penetrate through the opposite and of the fourth medication container 16F and thereby establish an airflow path through all four of the medication containers 16A, 16B, 16E, or 16F. It is to be appreciated that during dispensing, the upper delivery needle 26X and the lower delivery needle 26Y are slightly separated from one another. Accordingly, when the inhaler is activated, airflow is permitted to enter, via the lower delivery needle 26Y, and pass through each of the first, the second, the third and the fourth medication containers 16A, 16B, 16E and 16F, via the upper delivery needle 26X, and facilitate dispensing of all of the medication contained within the medication containers, as described herein.

It is to be appreciated that while some of the embodiments discussed above are provided with a bypass airflow which is achieved by the bypass vent passages 20V (see FIGS. 7A-7D, for example), other embodiments are not provided with any bypass vent passages (see FIGS. 19A-21C, for example). One advantage of the dry medication inhaler 10 being provided with a series of circumferentially arranged bypass vent passages is that bypass airflow tends to prevent any accumulation of the powder being dispensed from "holdup", i.e., collecting or accumulating on the inner surface of the mouthpiece chamber 12A in the upper portion of mouthpiece 12 and thus being prevented from being dispensed to the patient. In the embodiments having bypass vent passages, the bypass vent passages are designed so as to create a generally laminar airflow within the mouthpiece chamber 12A and such generally laminar airflow surrounds the power being dispensed from the outlet of the needle passage 12C and thereby generally causes the powder to also flow substantially as a laminar flow which is encased by the bypass airflow. Accordingly, for applications where "holdup" of the powder being dispensed is of concern, then the dry medication inhaler 10 will typically be provided with circumferentially arranged bypass vent passages, but for applications where "holdup" of the powder being dispensed is not of concern, then the dry medication inhaler 10 typically will not have; any circumferentially arranged bypass vent passages.

It must be recognized with regard to the above descriptions of possible implementations of an inhaler of the present invention that certain changes may be made in the above described improved medication inhaler, without departing from the spirit and scope of the invention herein involved. For example, while a presently preferred embodiment of the invention has been described and discussed in detail herein above, it must be recognized that different circumstances, such as medications have different particle characteristics, other features or combinations of features described herein above may comprise a preferred embodiment other than the exemplary presently preferred embodiment described herein above. It is therefore intended that all of the subject matter of the above description or shown in the accompanying drawings shall be interpreted merely as examples illustrating the inventive concept herein and shall not be construed as limiting the invention.

What is claimed is:

1. A multiple dose medication inhaler comprising:
   an inhaler body having:
     at least first and second axially aligned medication container chambers, the first medication container chamber for receiving a first medication container and the second medication container chamber for receiving a second medication container,
     at least one air passage connecting the first and the second medication container chambers with external air, and
   a mouthpiece axially engageable with the inhaler body and having:
     a mouthpiece chamber for communication with a patient's respiratory system, and
     a hollow medication delivery needle communicating with the mouthpiece chamber and extending toward the first and the second medication container chambers, the needle having at least first and second air/medication ports spaced along a sidewall of the medication delivery needle and formed in a surface of the sidewall for passing exterior air and medication from interior spaces of the first and the second medication containers, through the needle and to mouthpiece chamber when the first and second medication containers are located within the respective first and the second medication container chambers,
   the mouthpiece engaging with the inhaler body in
     a first position in which the needle extends toward the first and the second medication container chambers short of the first and the second medication containers located in the respective first and the second medication container chambers, and
     in a second position in which the needle axially traverses both the first and the second medication containers so that the at least first air/medication port in the needle is located within and communicates with the at least one air passage and the interior spaces of the first medication container when the first medication container is located in the first medication container chamber, and the at least second air/medication port in the needle is located within and communicates with the at least one air passage and the interior spaces of the second medication container, when the second medication container is located within the second medication container chamber.

2. The medication inhaler of claim 1, wherein the medication delivery needle comprises:
a hollow, tubular body, and
a pyramidal puncturing point closing an end of the hollow, tubular body, and
the body includes the at least first and second air/medication ports located along the body.

3. The multiple dose medication inhaler of claim 1, wherein:
the first medication container and the first medication container chamber both have a larger diameter than the second medication container and the second medication container chamber.

4. The multiple dose medication inhaler of claim 1, wherein:
the first medication container and the first medication container chamber are of generally equal diameter with the second medication container and the second medication container chamber.

5. The multiple dose medication inhaler of claim 1, further comprising:
a container spacer located between the first and the second medication containers,
the container spacer generally has a cylindrical shape with a diameter sized so as to be closely received in one of the first and the second medication container chambers and having concave axial faces generally shaped to conform with ends of the first and the second medication containers and an axial needle passage for accommodating passage of the medication delivery needle.

6. The multiple dose medication inhaler of claim 1, further comprising:
a container adapter located in one of the first and the second medication container chambers,
the container adapter generally has a cylindrical shape with a diameter sized so as to be closely received within and axially supported in one of the first and the second medication container chambers and includes a generally cylindrical container chamber which has an internal diameter so as to closely receive one of the first and the second medication containers which has a smaller diameter than that of the other of the first and the second medication containers, wherein the generally cylindrical container chamber supports the one of the first and the second medication containers which has a smaller diameter in axial alignment with the other of the first and the second medication containers,
the container adapter has an axial opening therethrough for accommodating passage of the medication delivery needle.

7. The multiple dose medication inhaler of claim 1, further comprising:
the inhaler body further having at least a third axially aligned medication container chamber for receiving a third medication container;
the hollow medication delivery needle further having at least a third air/medication port spaced along and located in a sidewall of the medication delivery needle for passing exterior air and medication from interior spaces of the third medication container, through the needle and to mouthpiece chamber when the third medication container is located within the third medication container chamber; and
the mouthpiece further engaging with the inhaler body such that the needle axially traverses the third medication container and the at least third air/medication port in the needle is located within and communicates with the at least one air passage and the interior spaces of the third medication container when the third medication container is located within the third medication container chamber.

8. The multiple dose medication inhaler of claim 7, further comprising:
the inhaler body further having at least a fourth axially aligned medication container chamber for receiving a fourth medication container;
the hollow medication delivery needle further having at least a fourth air/medication port spaced along and located in a sidewall of the medication delivery needle for passing exterior air and medication from interior spaces of the fourth medication container, through the needle and to mouthpiece chamber when the fourth medication container is located within the fourth medication container chamber; and
the mouthpiece further engaging with the inhaler body such that the needle axially traverses the fourth medication container and the at least fourth air/medication port in the needle is located within and communicates with the at least one air passage and the interior spaces of the fourth medication container when the fourth medication container is located within the fourth medication container chamber.

* * * * *